US009345567B2

(12) United States Patent  (10) Patent No.: US 9,345,567 B2
Sengun  (45) Date of Patent: May 24, 2016

(54) SYSTEMS, DEVICES, AND METHODS FOR SECURING TISSUE USING SNARE ASSEMBLIES AND SOFT ANCHORS

(75) Inventor: Mehmet Ziya Sengun, Canton, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 926 days.

(21) Appl. No.: 13/465,376

(22) Filed: May 7, 2012

(65) Prior Publication Data

US 2013/0296934 A1  Nov. 7, 2013

(51) Int. Cl.
*A61B 17/04* (2006.01)
*A61F 2/08* (2006.01)
(Continued)

(52) U.S. Cl.
CPC ............ *A61F 2/0811* (2013.01); *A61B 17/0401* (2013.01); *A61B 17/06166* (2013.01); *A61B 19/44* (2013.01); *A61B 2017/00336* (2013.01); *A61B 2017/00845* (2013.01); *A61B 2017/00849* (2013.01); *A61B 2017/042* (2013.01); *A61B 2017/0406* (2013.01);
(Continued)

(58) Field of Classification Search
CPC ............. A61B 17/0401; A61B 17/042; A61B 2017/0459; A61B 2017/0458; A61B 2017/0414; A61B 17/842; A61B 17/844; A61B 2017/042; A61B 2017/0422; A61B 2017/0424; A61B 2017/0406; A61B 2017/0475; A61B 2017/0474; A61B 2017/0477; A61B 2017/0618; A61B 2017/06185; A61B 2017/00849; A61B 2017/00862; A61B 2017/0496; A61B 2017/00592; A61B 2017/00845; A61B 2017/0417; A61B 2017/00336; A61B 17/06166; A61F 2002/0817; A61F 2002/0835; A61F 2002/0852; A61F 2002/0888; A61F 2/0811; D04G 1/00; D04G 1/04; D04G 1/06; D04G 1/08
See application file for complete search history.

(56) References Cited

U.S. PATENT DOCUMENTS 2,566,625 A  9/1951 Nagelmann
2,600,395 A  6/1952 Domoj et al.
(Continued)

FOREIGN PATENT DOCUMENTS

AU  2008229746 A1  10/2008
CA  2772500 A1  9/2013
(Continued)

OTHER PUBLICATIONS

[No Author Listed] Gryphon Brochure. DePuy Mitek. 2 pages (undated).
(Continued)

*Primary Examiner* — Jonathan W Miles
*Assistant Examiner* — Kendra Obu

(57) ABSTRACT

Systems, devices, and methods are provided for securing soft tissue to bone. One exemplary embodiment of a surgical soft tissue repair device includes a snare assembly coupled to a soft anchor in which the soft anchor has a first, unstressed configuration that can be used to insert the anchor into bone and a second, anchoring configuration that can be used to fixate the anchor in the bone. The snare assembly can be configured to actuate the anchor from the first configuration to the second configuration, and it can also be used to engage and approximate tissue by drawing the tissue closer to the anchor fixated in the bone. The snare assembly can be used in conjunction with a number of different anchor configurations, and other exemplary systems, devices, and methods for use with soft tissue repair are also provided.

23 Claims, 13 Drawing Sheets

(51) Int. Cl.
*A61B 17/06* (2006.01)
*A61B 19/00* (2006.01)
*A61B 17/00* (2006.01)

(52) U.S. Cl.
CPC ...... *A61B 2017/0414* (2013.01); *A61B 2017/0417* (2013.01); *A61B 2017/0458* (2013.01); *A61B 2017/0475* (2013.01); *A61B 2017/06185* (2013.01); *A61B 2019/444* (2013.01); *A61F 2002/0852* (2013.01); *A61F 2002/0888* (2013.01)

(56) References Cited

U.S. PATENT DOCUMENTS

| | | |
|---|---|---|
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |

(56) References Cited

U.S. PATENT DOCUMENTS

| | | | |
|---|---|---|---|
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,419,769 B2 | 4/2013 | Thal |
| 8,545,535 B2 | 10/2013 | Hirotsuka et al. |
| 8,608,758 B2 | 12/2013 | Singhatat et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 | 6/2015 | Sengun |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0187577 A1 | 8/2005 | Selvitelli et al. |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0190815 A1 | 8/2011 | Saliman |
| 2011/0208240 A1 | 8/2011 | Stone et al. |
| 2011/0213416 A1 | 9/2011 | Kaiser |
| 2011/0238111 A1 | 9/2011 | Frank |
| 2011/0264141 A1* | 10/2011 | Denham ............ A61B 17/0401 606/232 |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2014/0081324 A1 | 3/2014 | Sengun |
| 2014/0188163 A1 | 7/2014 | Sengun |
| 2014/0188164 A1 | 7/2014 | Sengun |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |

(56) References Cited

U.S. PATENT DOCUMENTS

| | | |
|---|---|---|
| 2015/0238183 A1 | 8/2015 | Sengun |
| 2015/0245832 A1 | 9/2015 | Sengun |
| 2015/0297214 A1 | 10/2015 | Hernandez et al. |

FOREIGN PATENT DOCUMENTS

| | | |
|---|---|---|
| EP | 0870471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| JP | 2000-5121193 A | 9/2000 |
| WO | 9519139 A1 | 7/1995 |
| WO | 9717901 A1 | 5/1997 |
| WO | 9811825 A1 | 3/1998 |
| WO | 98/42261 A1 | 10/1998 |
| WO | 01/06933 A2 | 2/2001 |
| WO | 03/022161 A1 | 3/2003 |
| WO | 2007/109769 A1 | 9/2007 |

OTHER PUBLICATIONS

Extended European Search Report for Application No. 13185425.9 issued Dec. 16, 2013 (9 Pages).

Extended European Search Report for Application No. 13199724.9 issued Apr. 4, 2014 (6 Pages).

EP Search Report for Application No. 11190159.1 issued Feb. 21, 2012. (8 pages).

EP Search Report for Application No. 11190157.5 issued Feb. 27, 2012. (8 pages).

Dahl et al., Biomechanical characteristics of 9 arthroscopic knots. Arthroscopy. Jun. 2010;26(6):813-8.

[No Author Listed] Arthroscopic Knot Tying Manual 2005. DePuy Mitek.

Kemnitzer et al., Handbook of biodegradable Polymers. Eds. Domb et al. Hardwoof Acad. Press. 1997;251-72.

Cohn et al., Biodegradable PEO/PLA block copolymers. J Biomed Mater Res. Nov. 1988;22(11):993-1009.

Cohn et al., Polym Preprint. 1989;30(1):498.

Allock, The Encyclopedia of Polymer Science, vol. 13, pp. 31-41, Wiley Intersciences, John Wiley & Sons, 1988.

Vandorpe et al., Handbook of Biodegradable Polymers, edited by Domb, et al., Hardwood Academic Press, pp. 161-182 (1997).

Heller, Handbook of Biodegradable Polymers, edited by Domb, et al., Hardwood Academic Press, pp. 99-118 (1997).

Extended European Search Report for Application No. 11190159.1 issued Jul. 6, 2012. (11 pages).

Extended European Search Report for Application No. 11190157.5 issued Jul. 6, 2012. (10 pages).

International Search Report for Application No. PCT/US2011/067119, mailed Jun. 4, 2012. (6 pages).

Extended European Search Report for Application No. 13166905.3 issued Aug. 13, 2013 (9 Pages).

Extended European Search Report for Application No. 13166907.9, issued Aug. 1, 2013 (6 pages).

Extended European Search Report for Application No. 13166908.7, issued Aug. 23, 2013 (8 pages).

Extented European Search Report for Application No. 11195100.0 issued Oct. 17, 2012. (7 pages).

[No Author Listed] Versalok Anchor. Brochure. DePuy Mitek, a Johnson & Johnson company, 92 pages, 2007.

Japanese Office Action for Application No. 2011-281088, issued Nov. 10, 2015 (4 pages).

* cited by examiner

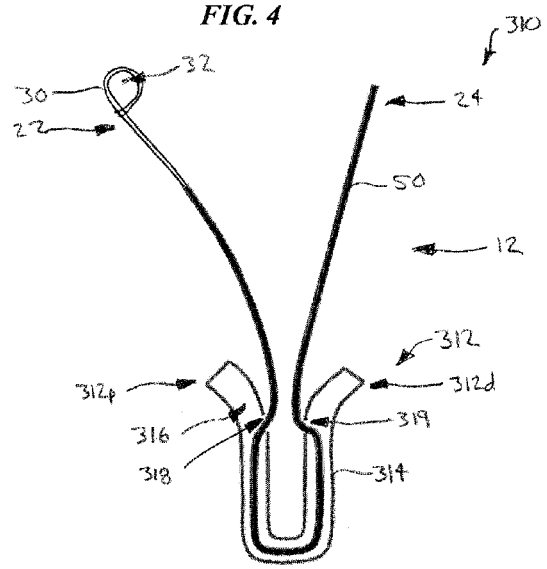
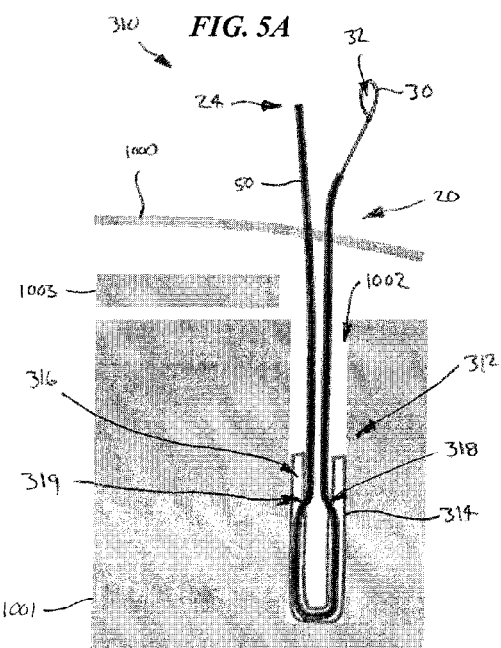
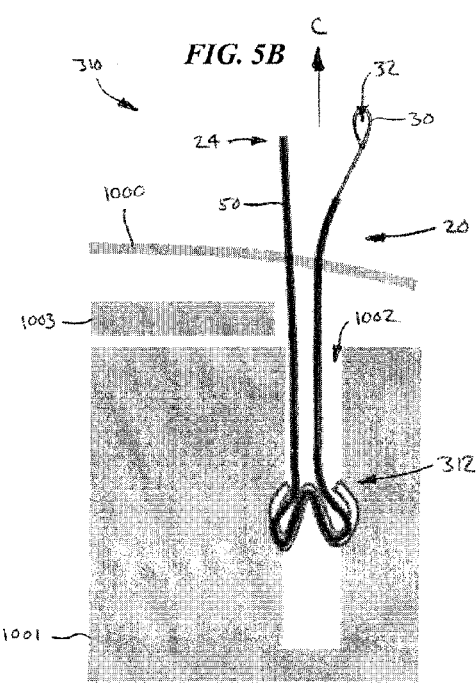

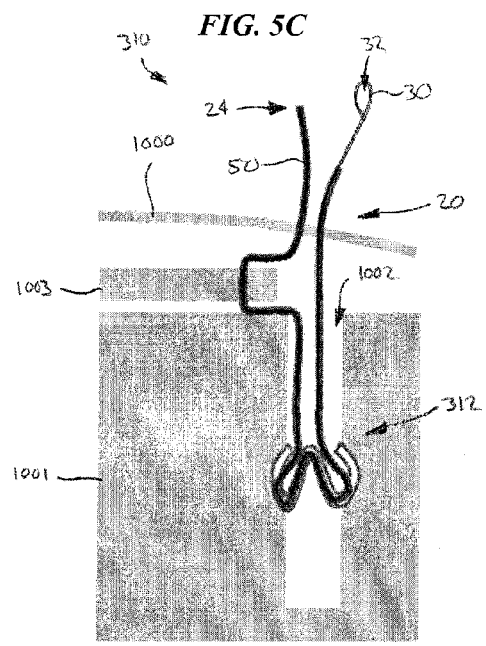
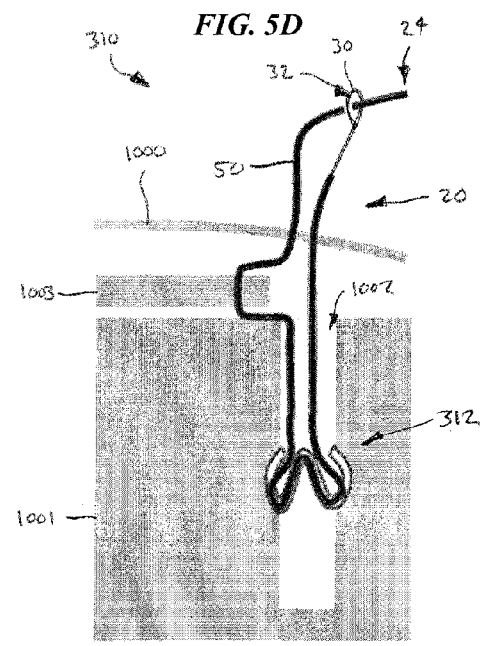
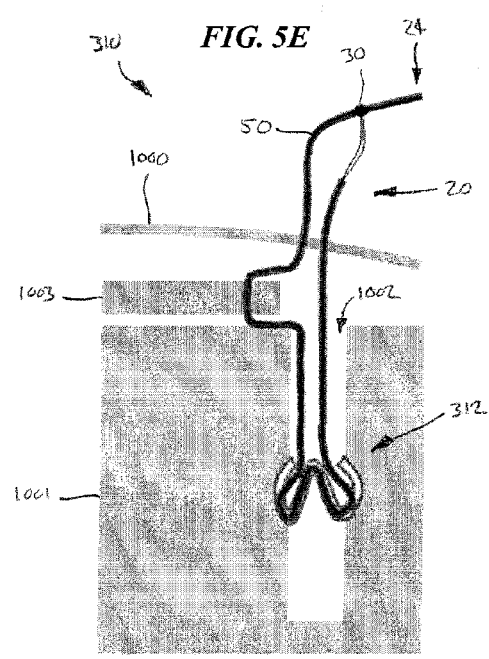
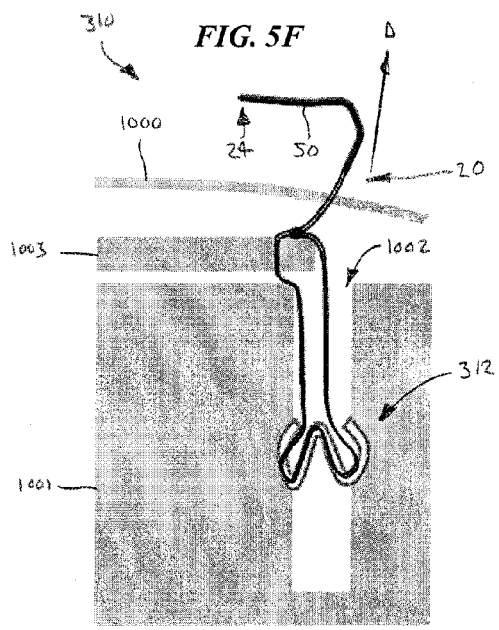

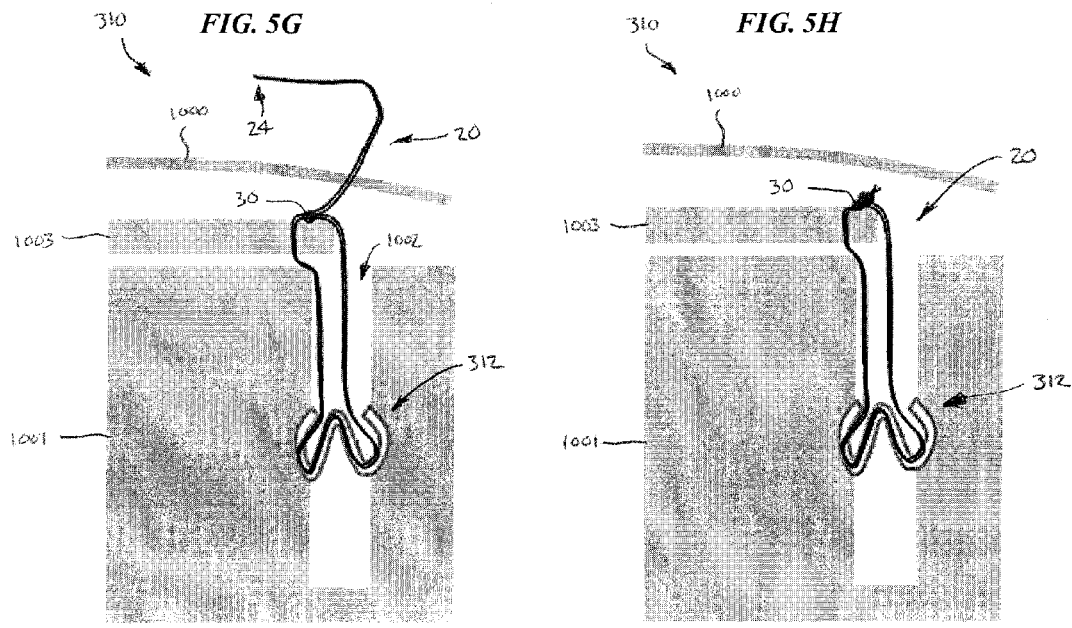
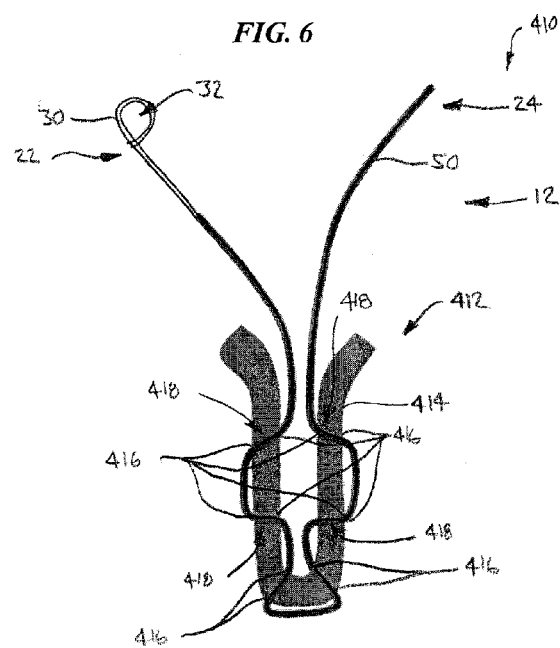

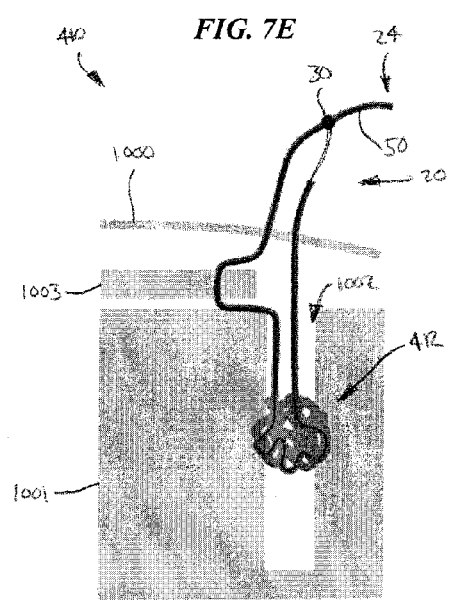
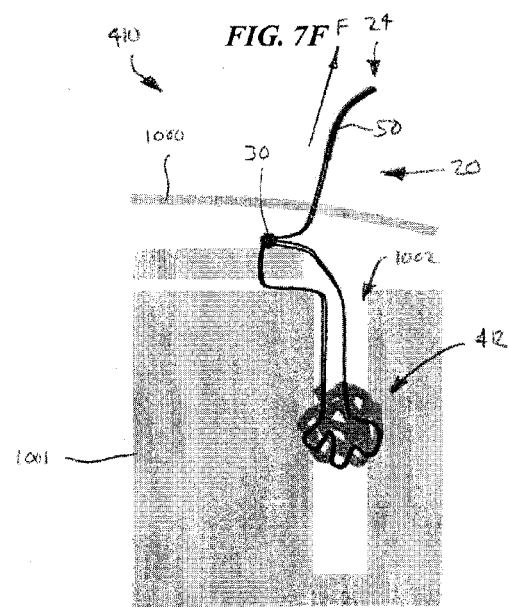
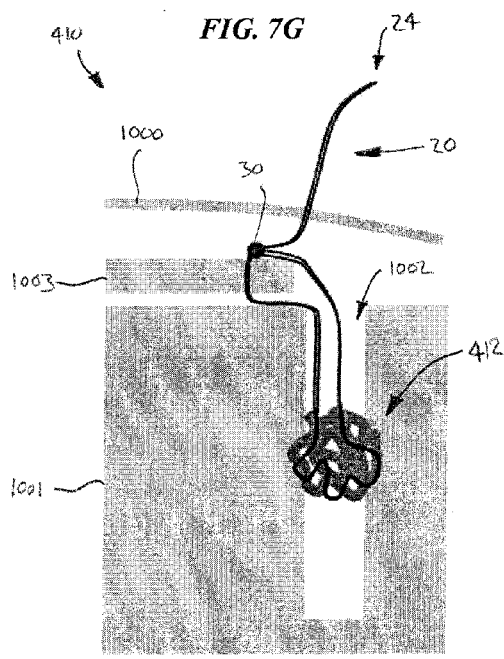
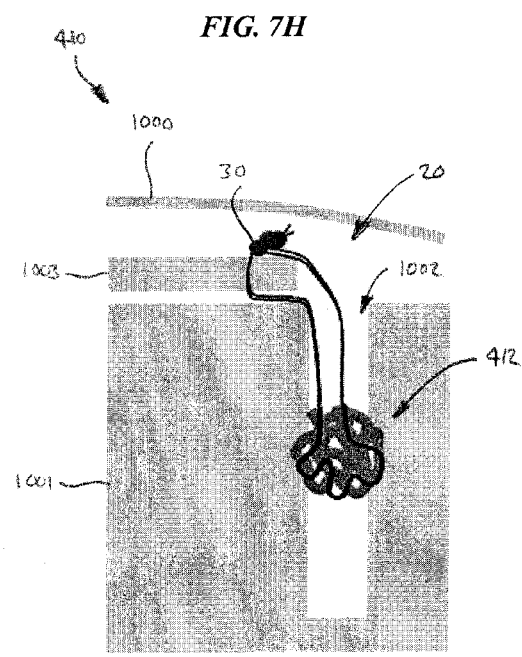

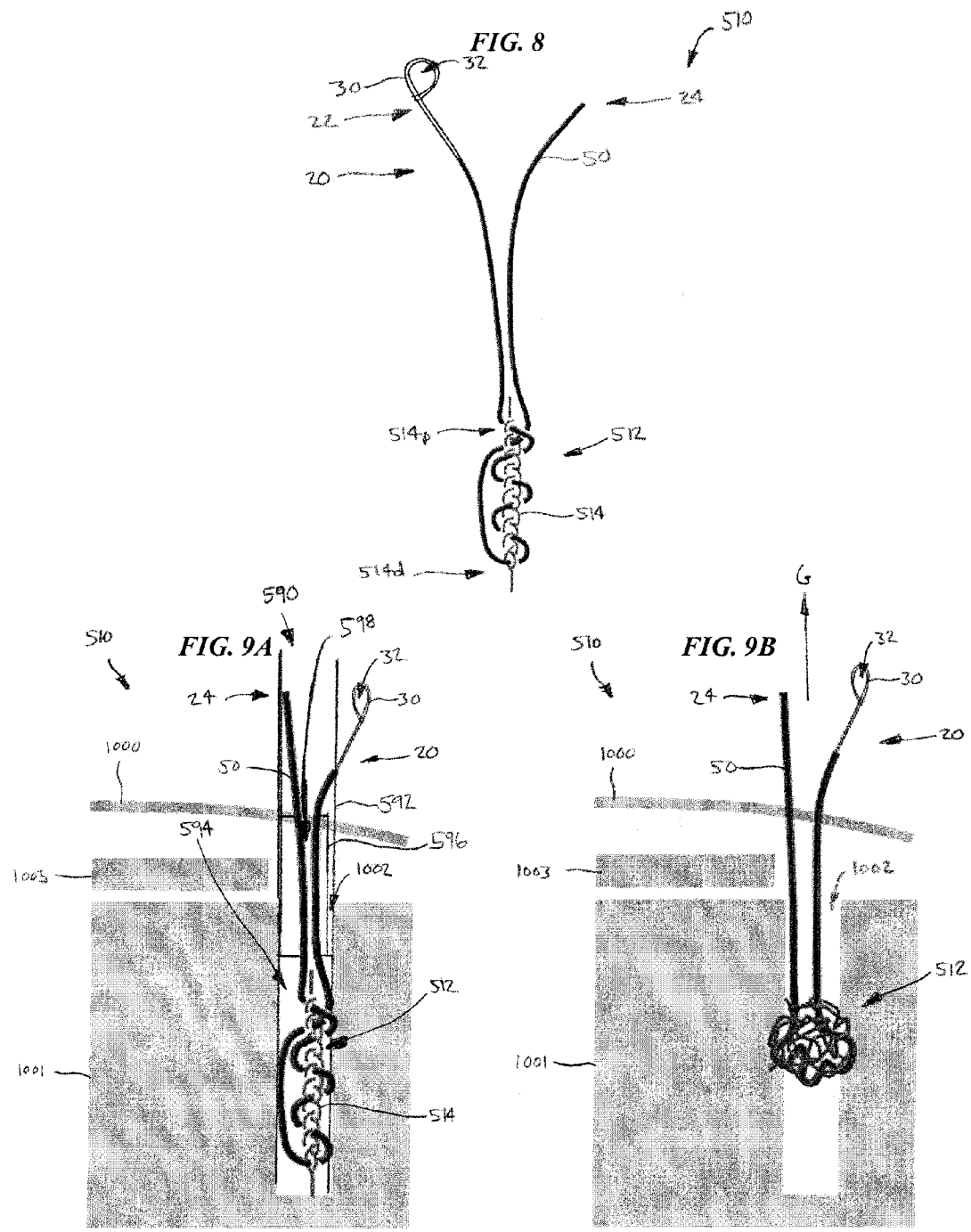

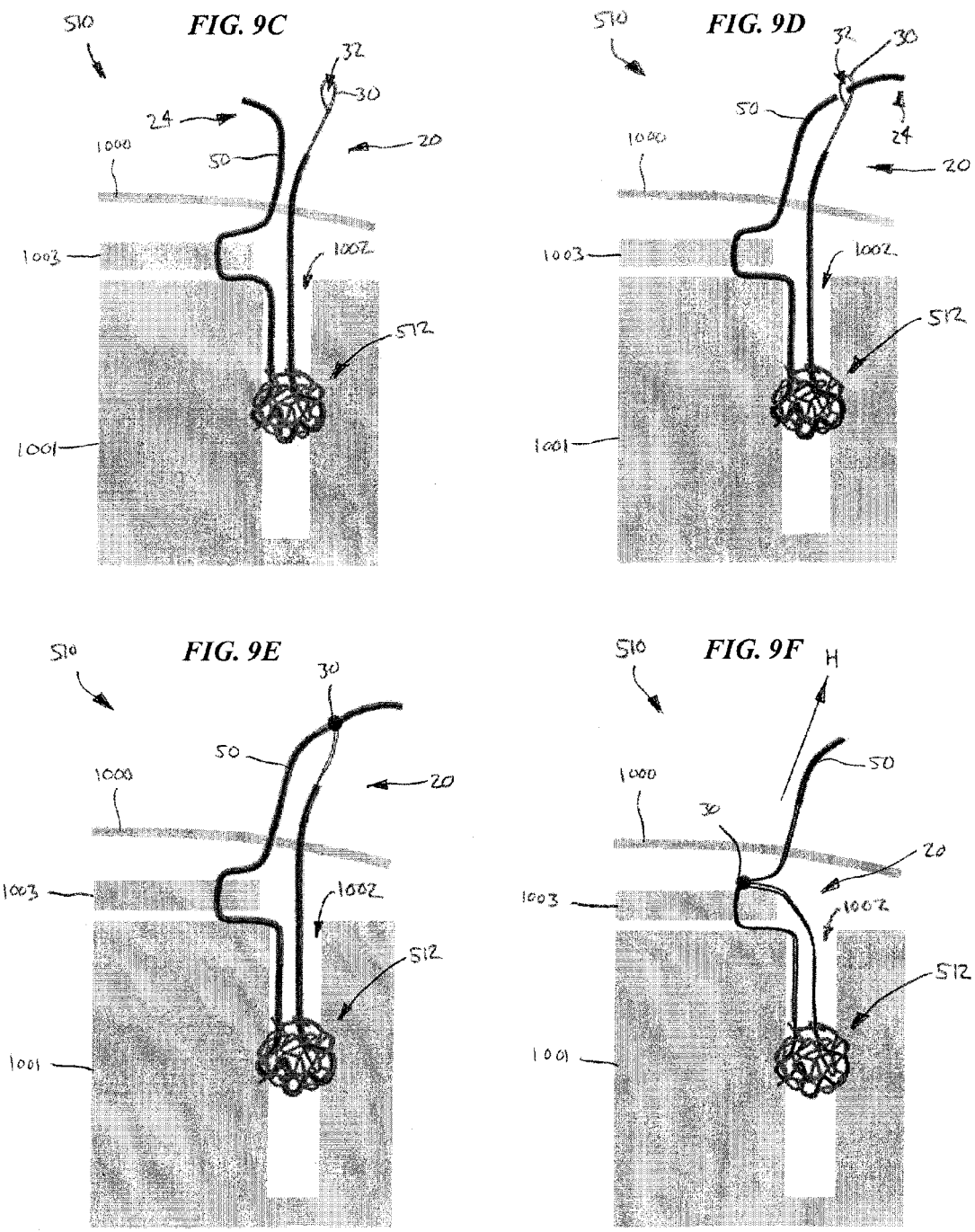

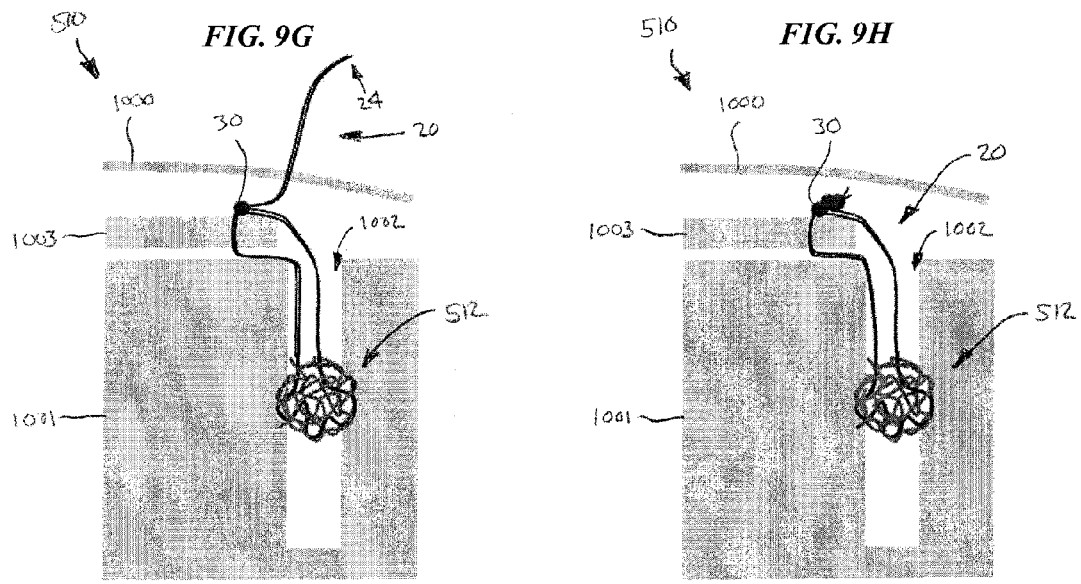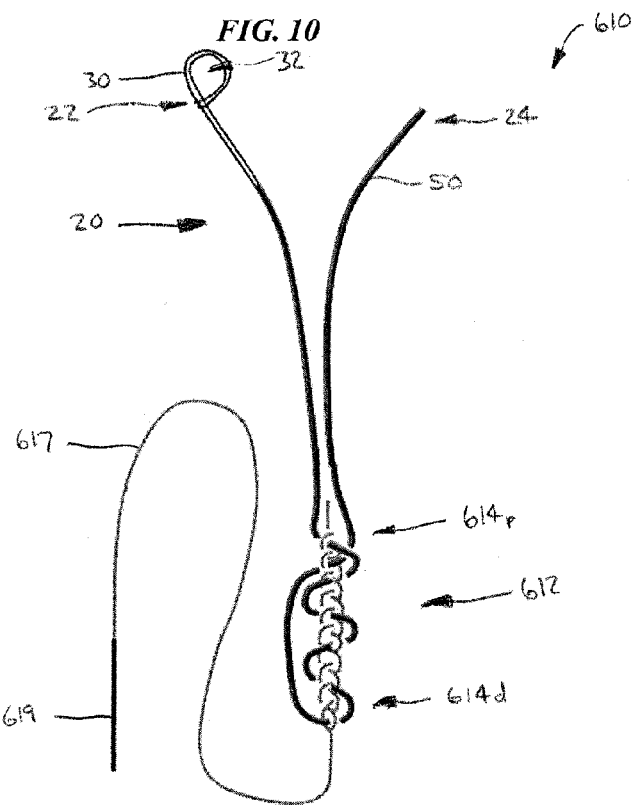

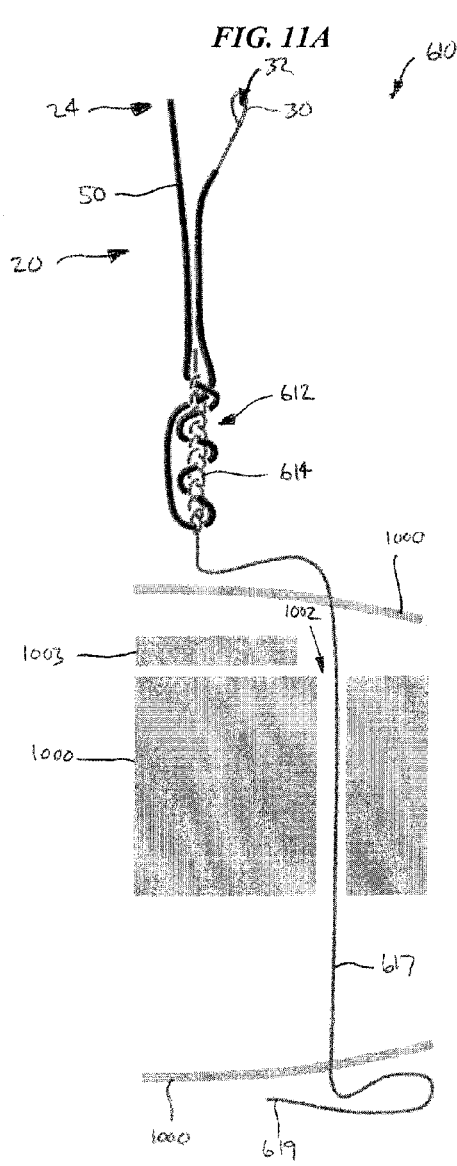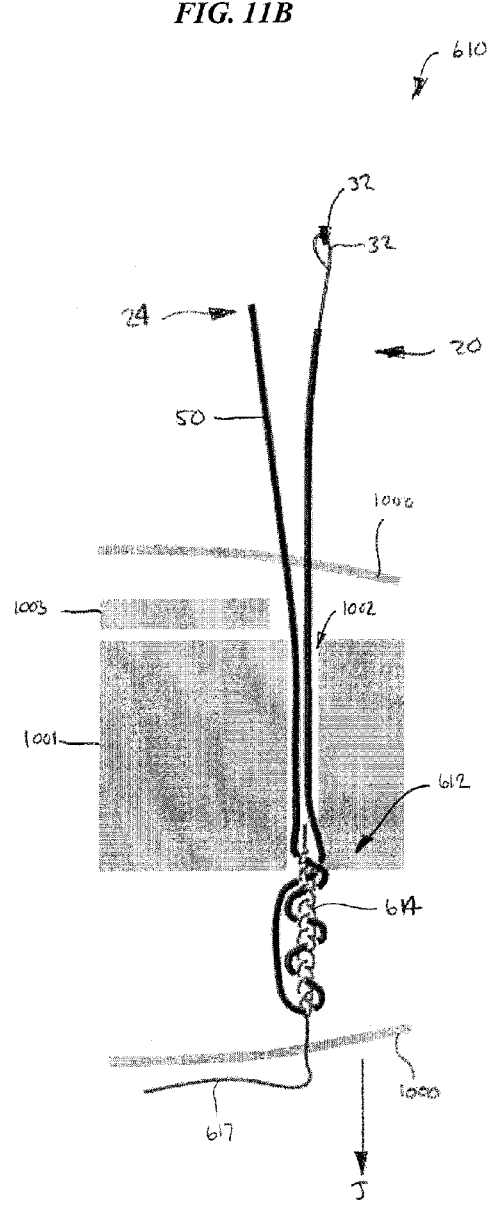

SYSTEMS, DEVICES, AND METHODS FOR SECURING TISSUE USING SNARE ASSEMBLIES AND SOFT ANCHORS

FIELD

The present disclosure relates to systems, devices, and methods for securing soft tissue to bone, and more particularly relates to securing soft tissue while minimizing or eliminating the tying of knots to tension and secure the tissue.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate suture-to-anchor fixation.

Arthroscopic knot tying is commonly practiced in shoulder rotator cuff and instability procedures. Typically, an anchor loaded with suture is first attached to bone. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Surgeons typically tie the suture ends using a surgical sliding knot such as the Tennessee Slider or Duncan Loop. After advancing the knot distally to tighten the loop, a number of additional half hitches or other knots are tied in an effort to secure the new location of the sliding knot. The additional knots are needed because a conventional sliding knot used in current repair constructs does not provide the necessary protection against loosening or slippage, especially when tension is placed primarily on the limbs of the loop. The generally accepted practice is to follow the sliding knot with at least three reversed half hitches on alternating posts of the suture.

Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. In addition to this "loop security" problem, conventional knots typically have an overall size that can be obstructive or intrusive, especially in tight joints, which may damage cartilage or other tissue by abrasion with the knot.

Suture anchor systems with sliding and locking knots for repairing torn or damaged tissue include U.S. Pat. No. 6,767, 037 by Wenstrom, Jr. Other suture anchor systems suited especially for meniscal repair are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767. Screw-type anchors normally require anchor attachment before operating sutures, which can lead to challenges related to the connection between the suture and the tissue.

There are a number of suture implant systems which proclaim to be "knotless," that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors that capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042. Other systems having clamps or other locking mechanisms include U.S. Pat. No. 5,702,397 by Goble et al. and U.S. Patent Application Publication No. 2008/0091237 by Schwartz et al. Present, so-called "knotless" designs, however, generally suffer from inadequate suture-to-anchor fixation and/or inadequate anchor-to-bone fixation, among other deficiencies.

It is therefore desirable to provide systems, devices, and methods for use in soft tissue repair that are robust and strong, yet minimize or eliminate the number and size of knots to be tied by a surgeon, particularly during arthroscopic repair procedures. It is also desirable to provide systems, devices, and methods that minimize the number of components a system needed to secure an anchor in bone and approximate tissue to that bone. There is also a need for suture anchors and methods of deploying such anchors that minimizes the surgical trauma associated with the implantation of an anchor of a given size.

SUMMARY

Systems, devices, and methods are generally provided for securing soft tissue to bone. In one exemplary embodiment a surgical soft tissue repair device includes a snare assembly coupled to a soft anchor. The soft anchor can be formed of a flexible construct with a plurality of openings formed therein. The anchor can be configured to have a first, unstressed configuration, for example to insert the anchor into a bone, and a second, anchoring configuration to fix the anchor to the bone. The anchor can have a first length and a first diameter in the first configuration and a second length that is less than the first length and a second diameter that is greater than the first diameter. The snare assembly can have a collapsible snare at one end and at least one elongate filament extending therefrom. The filament includes a terminal end that is opposite the collapsible snare and the filament can pass through openings in the soft anchor to couple the snare assembly to the soft anchor such that the soft anchor is at an intermediate location on the elongate filament between the snare and the terminal end. The soft anchor and snare can be configured such that the soft anchor is reconfigurable from its first, unstressed configuration to its second, anchoring configuration by the application of tension to the filament.

In some embodiments the soft anchor can be a cannulated suture with a central lumen. Further, the plurality of openings can include a first opening on a distal portion of the soft anchor and a second opening on a proximal portion of the soft anchor, with each of the two openings being in communication with the central lumen. In one, non-limiting configuration, the filament can pass into the second opening, through the lumen, and out of the first opening. In some embodiments the first and second openings can be on the same side of the soft anchor.

In some other embodiments the soft anchor can include a plurality of transverse bores extending therethrough along the length of the soft anchor. In such an embodiment, the anchor can be cannulated or non-cannulated. The plurality of openings can include opposed paired openings, and each opposed paired opening can communicate with one of the transverse bores. In one, non-limiting configuration, the anchor can include at least four transverse bores and the filament can pass into and out of each transverse bore through the opposed paired openings.

In yet some other embodiments the soft anchor can be a crocheted suture anchor, and the filament can extend through openings defined between filament limbs of the crocheted suture anchor along the length thereof.

In its anchoring configuration, the soft anchor can have a diameter that is at least about 20% greater than its diameter in the unstressed configuration. The snare assembly can be formed of a double filament loop such that the filament has first and second filament limbs. A removable, flexible sleeve can be included as part of the device to removably encapsulate at least a portion of the filament.

In another exemplary embodiment a surgical soft tissue repair device includes an anchor, a snare assembly, and a connecting filament coupled to the snare assembly and effective to connect the snare assembly to the anchor. The anchor can be configured to be fixated in bone, and it can have at least one bore extending therethrough. The snare assembly can have a collapsible snare at one end and at least one elongate filament extending therefrom, with the filament having a terminal end that is opposite the collapsible snare. The connecting filament can be disposed in the bore or on a side of the bore distal to the snare assembly, and can be configured to be secured to the anchor such that the anchor is positioned at an intermediate location on the elongate filament between the collapsible snare and the terminal end.

One exemplary embodiment of a surgical repair method includes inserting a flexible anchor into a hole in a bone at a location proximate to detached soft tissue. The anchor can have first and second configurations, with the first configuration having a first length and a first diameter and the second configuration having a second length that is less than the first length and a second diameter that is greater than the first diameter. The anchor can be coupled to a snare assembly that passes through at least a portion of the anchor, with the snare assembly having a collapsible snare at one end thereof and at least one elongate filament extending therefrom. The elongate filament can have a terminal end that is opposite the collapsible snare. The method can also include tensioning the filament to move the anchor from the first configuration to the second configuration to fix the anchor relative to bone, passing at least one of the snare and the terminal end of the elongate filament through at least a portion of the detached tissue, inserting the terminal end of the filament through the snare, collapsing the snare around the filament, and sliding the collapsed snare toward the soft tissue to apply tension to filament between the anchor and the tissue to bring the tissue into proximity with the bone.

The first and second configurations can be defined by the second length being at least about 50% less than the first length. The first and second configurations can also be defined such that the second diameter is at least about 20% greater than the first diameter. In some embodiments the flexible anchor can be a cannulated anchor with a lumen extending therethrough. Such an anchor can include a first opening at its proximal end and a second opening at its distal end, with each of the first and second openings being in communication with the lumen. In some embodiments the flexible anchor can have one or more plurality of bores extending transversely therethrough along the length of the flexible anchor.

BRIEF DESCRIPTION OF DRAWINGS

This invention will be more fully understood from the following detailed description taken in conjunction with the accompanying drawings, in which:

FIG. 4 is a schematic view of one exemplary embodiment of a surgical soft tissue repair device that includes the snare assembly of FIG. 1 and one embodiment of an anchor;

FIGS. 5A-5H are sequential views of one exemplary embodiment for using the surgical soft tissue repair device of FIG. 4 to secure tissue to bone;

FIG. 6 is a schematic view of another exemplary embodiment of a surgical soft tissue repair device that includes the snare assembly of FIG. 1 and another embodiment of an anchor;

FIGS. 7A-7H are sequential views of one exemplary embodiment for using the surgical soft tissue repair device of FIG. 6 to secure tissue to bone;

FIG. 8 is a schematic view of still another exemplary embodiment of a surgical soft tissue repair device that includes the snare assembly of FIG. 1 and still another embodiment of an anchor;

FIGS. 9A-9H are sequential views of one exemplary embodiment for using the surgical soft tissue repair device of FIG. 8 to secure tissue to bone;

FIG. 10 is a schematic view of yet another exemplary embodiment of a surgical soft tissue repair device that includes the snare assembly of FIG. 1 and yet another embodiment of an anchor; and FIGS. 11A-11J are sequential views of one exemplary embodiment for using the surgical soft tissue repair device of FIG. 10 to secure tissue to bone.

DETAILED DESCRIPTION

Figure 1:
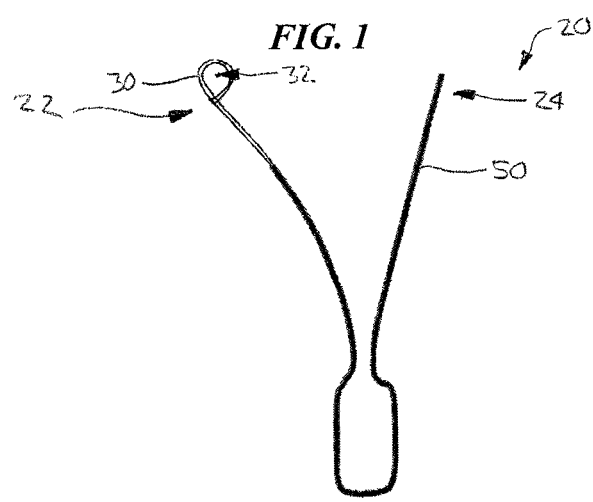
FIG. 1 is a schematic view of one exemplary embodiment of a snare assembly for use as part of a surgical soft tissue repair device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction of movement, these arrows are illustrative and in no way limit the direction the respective component can or should be moved. A person skilled in the art will recognize other ways and directions for creating the desired result. Additionally, a number of terms may be used throughout the disclosure interchangeably but will be understood by a person skilled in the art. By way of non-limiting example, the terms suture and filament may be used interchangeably.

Systems, devices, and methods for soft tissue repair are generally provided and they generally involve the use of surgical filaments that are configured in a variety of manners to minimize and/or eliminate the tying of knots during a surgical procedure. The systems and devices described herein provide superior strength for use in a number of different surgical procedures, such as rotator cuff and instability repair procedures and other types of tendon and tissue repair procedures. The systems, devices, and methods described herein also allow for constructs used to repair tissue to be made completely of flexible members, thereby minimizing or eliminating trauma that can result from using harder materials for tissue repair. The systems and devices provided herein further allow for both improved and new procedures for soft tissue repair. For example, the systems and devices provided herein can be used to both secure an anchor in bone and draw tissue toward the bone for attachment thereto.

FIG. 1 illustrates one exemplary embodiment of a snare assembly 20 for use in conjunction with a number of different configurations of soft anchors, some non-limiting examples of which are provided and discussed below with respect to FIGS. 4-11J. As shown in FIG. 1, the snare assembly 20 can be generally flexible, can include a snare 30 formed on a first end 22, and can have a terminal end 24 opposite the first end 22, with an intermediate portion extending therebetween. The terminal end 24 can be configured to pass through an opening 32 in the snare to create a tensionable construct so the snare assembly can draw two or more objects, such as tissue and bone, closer together, as described in greater detail below. Further, in embodiments in which the snare assembly 20 is coupled to an anchor having both an unstressed configuration for insertion and an anchoring configuration for placement of the anchor in bone, the snare assembly 20 can be used to actuate the transition of the anchor from its unstressed configuration to its anchoring configuration, as also described in greater detail below.

Optionally, a flexible sleeve 50 can be provided for encapsulating at least a portion of the assembly 20. As shown in FIG. 1, the sleeve encapsulates a portion of the assembly 20 starting at the terminal end 24 and extending toward the first end 22. In other embodiments the sleeve can extend more proximal than the terminal end 24. A configuration of this nature can aid a surgeon in pulling the snare assembly 20 through a portion of the body by providing extra length onto which he or she can grasp. Preferably, once the assembly 20 is implanted, the sleeve 50 can extend outside of a body as well as outside of a cannula placed in the body so the sleeve 50 can be easily removed. The sleeve 50 can have a generally cylindrical configuration and can be flexible to allow it to bend as shown in various embodiments provided herein. The sleeve 50 can be useful when passing the assembly 20 through obstructions such as an anchor and/or tissue for a number of reasons. The sleeve 50 can be configured to have a smoother surface that is better configured to pass through a soft anchor and tissue, thus reducing the possibility of fraying the soft anchor or causing trauma to the tissue. Still further, because the sleeve 50 can encapsulate a plurality of filament limbs, the sleeve 50 can ease filament management by maintaining the filaments within the enclosed sleeve 50. The sleeve 50 can be removable, and thus it can be removed at any time during the procedure, or at the conclusion of the procedure.

Figure 2A:
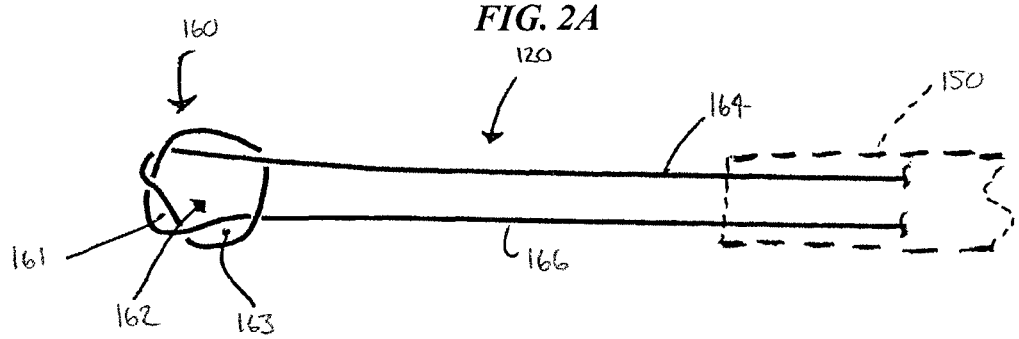
FIG. 2A is a schematic view of a snare assembly having a noose formed therein with first and second filament limbs extending to a second end.
Figure 2B:
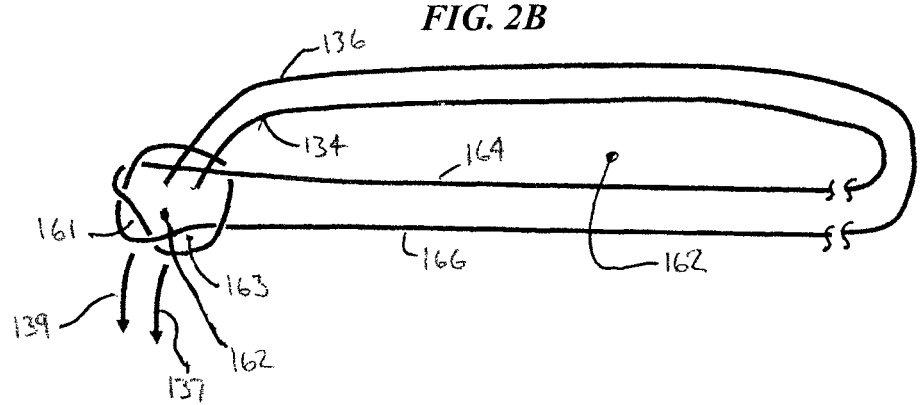
FIGS. 2B and 2C are sequential views of the snare assembly of FIG. 2A with the first and second filament limbs passed through the noose to form a snare or cinch noose.
Figure 2C:
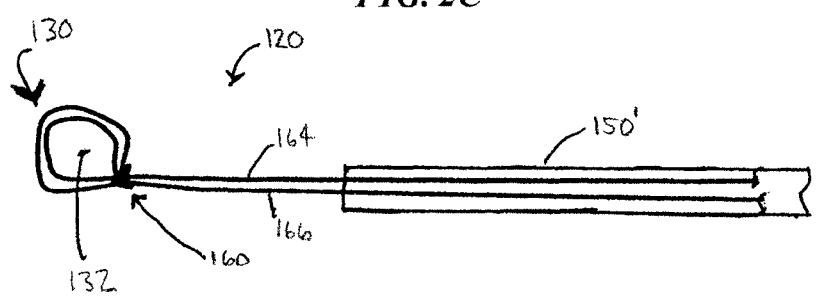

FIGS. 2A-2C illustrate one exemplary method of forming a snare assembly. As shown in FIG. 2A, the snare assembly 120 can be a filament having a noose 160 and noose limbs 164, 166. The noose 160 defines a central opening 162 and secondary openings 161 and 163 formed from a half hitch plus one additional throw of limb 166 through central opening 162. A flexible sleeve 150 is shown in phantom as it optionally encapsulates a portion of limbs 164 and 166 in certain constructions, as described in more detail below.

FIGS. 2B and 2C more particularly illustrate the formation of a cinch noose or snare 130 in an improved cinch noose construct or snare assembly 120, having an opening 132. The ends of free filament limbs 134 and 136 of the filament are passed through central opening 162, as represented by arrows 137 and 139 in FIG. 2B, which draws noose limbs 134 and 136 therethrough. Noose 160 is then tightened, as shown in FIG. 2C, to form a slidable knot for the snare 130. Alternatively, if a sleeve 150, as shown in FIG. 2A, or a sleeve 150', as shown in FIG. 2C, is not utilized, or if such sleeve is removed after being passed through tissue to be tensioned, then one or both of free limbs 134, 136 can be passed through one or both of the openings 161, 163.

Joining together at least the free filament limbs improves suture management and reduces the possibility of suture entanglement or damage by instruments, especially when passed through a cannula. For example, a surgeon or other user need only grasp and pass one sleeve 150 through the noose 160 to thereby manipulate the free filament limbs 134, 136 as a single unit.

Figure 3A:
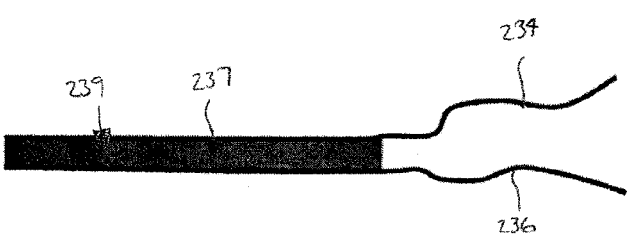
FIGS. 3A-3D are sequential views of another exemplary embodiment for forming a snare assembly having a snare at a first end and first and second filament limbs extending to a second end.
Figure 3B:
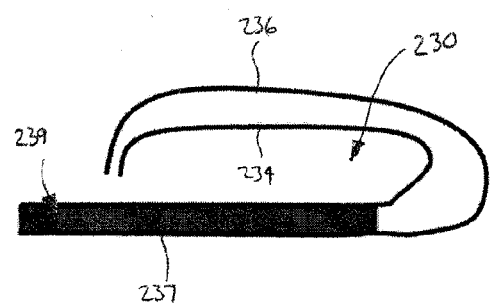
Figure 3C:
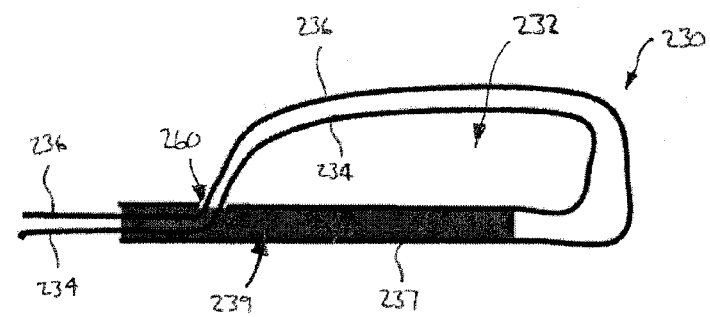
Figure 3D:
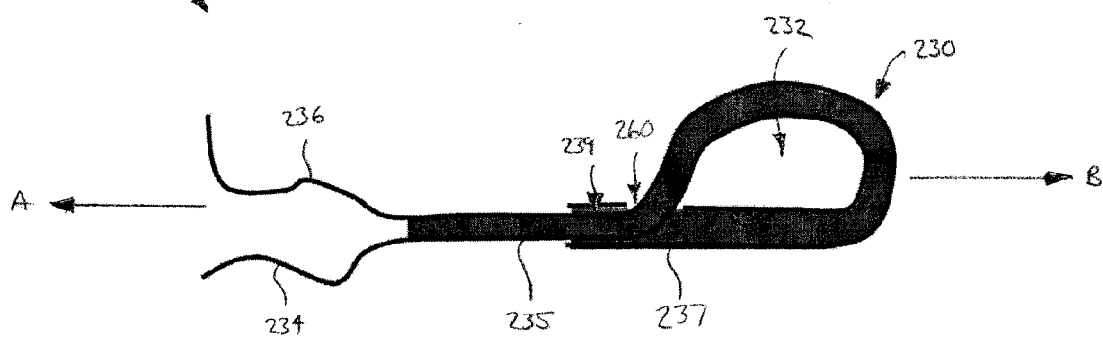

FIGS. 3A-3D illustrate another exemplary method of forming a snare assembly 220 having a snare 230 and a coaxial sliding neck 235 for use in a surgical repair construct. In this exemplary embodiment, the snare 230 is formed from a bifurcated suture filament having a tubular portion 237 with a core removed therefrom to form a cannulated portion 239 and first and second terminal limbs 234, 236. As shown in FIG. 3B, the terminal limbs 234, 236 can be curled back toward the tubular portion 237 to form a loop having an opening 232 that defines the snare 230. As shown in FIG. 3C, a bore 260 can be formed on a side of the tubular portion 237 and the terminal limbs 234, 236 can be placed into the cannulated tubular portion 239 through the bore 260. Ends of the terminal limbs 234, 236 can be fed through the cannulated portion 239, and as shown in FIG. 3D, the terminal limbs 234, 236 can be pulled distally (direction A in FIG. 3D) through the tubular portion 237 such that the tubular portion 237 is fed through itself. Accordingly, the snare 230 can be collapsed by tensioning the limbs 234, 236 and/or coaxial sliding neck 235 in approximately a first direction A, and the snare 230 can be expanded by applying a force to the snare 230 in approximately a second, opposite direction B, which pulls the limbs 234, 236 towards the snare 230. Passing the filament through itself to form a coaxial sliding neck allows the filament to have a low profile that minimizes the amount of space the construct consumes in the body and that minimizes and/or eliminates trauma associated with passing the filament through tissue.

A person having skill in the art will recognize a number of other ways that a snare for use in snare assemblies can be created and used in conjunction with the teachings herein. For example, a number of different sliding knots can be used to form snares, including but not limited to a Buntline Hitch, a Tennessee Slider, a Duncan Loop, a Hangman's Noose, and a coaxial sliding neck. To the extent the sliding knot used to form a snare affects the operation of the snare, for instance whether a limb is pulled through a knot to change the position of the knot or a knot is slid along a limb to change the position of the knot, a person skilled in the art would be able to adapt these types of knots for use with the teachings of the present invention without departing from the spirit of the present disclosure. As described herein, unless otherwise designated, a knot used to form a snare is movable away from the terminal end of the snare assembly to collapse the snare and towards the terminal end to increase a size of the snare.

The snare assemblies 20, 120, 220 can be made of any suitable flexible material, for instance a filament, including a cannulated filament, a braided filament, and a mono filament. The type, size, and strength of the flexible material can depend, at least in part, on the type of anchor with which it is used, any obstructions through which the snare assembly may pass, and the type of procedure in which it is used. In one exemplary embodiment the flexible material is a #2 filament (about 23 gauge to about 24 gauge), such as an Orthocord™ filament that is commercially available from DePuy Mitek, Inc or Ethibond™ filament available from Ethicon, Inc. Generally the filament is relatively thin to minimize any trauma to tissue through which it passes. In some embodiments the filament can have a size between about a #5 filament (about 20 gauge to about 21 gauge) and about a #5-0 filament (about 35 gauge to about 38 gauge). The Orthocord™ #2 filament can be useful because it has a braided configuration, which allows other components, including the filament itself, to pass through subcomponents of the braid without causing damage to the filament. Filaments configured to allow for a cannulated configuration, such as by removing a core therefrom or having a pre-formed cannulated configuration, can also be used. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. Further, a length of filaments used to form the snare assemblies 20, 120, 220 can be in the range of about 15 centimeters to about 125 centimeters, and in one embodiment it can be about 60 centimeters.

In embodiments that include a flexible sleeve, such as the embodiments shown in FIGS. 1, 2A and 2C, the sleeve 50, 150, 150' can be made from a wide variety of biocompatible flexible materials, including a flexible polymer or a filament. In one embodiment, the sleeve is made of a polymeric material. In another embodiment, the sleeve is a flexible filament, such as a braided suture, for example Ethibond™ #0 filament or Orthocord™ #2 filament, which is typically braided at sixty picks per 2.54 centimeters. For use as a sleeve, a more relaxed braid of approximately thirty to forty picks per 2.54 centimeters is preferred, more preferably about 36 picks per 2.54 centimeters. If the sleeve material is formed about a core, preferably that core is removed to facilitate insertion of the filament limbs, which may themselves be formed of typical suture such as Orthocord™ #0 suture or #2 suture braided at sixty picks per 2.54 centimeters. Additional convenience can be provided by perceptible indicators on the sleeve such as different markings, colors, diameters, braid or design patterns, or other tactile or visual indicia, especially if multiple tissue attachments or anchors are utilized.

A length and diameter of the sleeve 50, 150, 150' can depend, at least in part, on the size and configuration of the components of the device with which it is used, the obstructions through which the sleeve may pass, and the surgical procedure in which it is used. In any event, the sleeve is typically of a size such that it can pass atraumatically through tissue. In embodiments in which the sleeve is a filament, a size of the sleeve can be in the range of about a #5 filament (about 20 gauge to about 21 gauge) to about a #2-0 filament (about 28 gauge), and in one embodiment the size can be about a #0 filament (about 26 gauge to about 27 gauge). A person having skill in the art will recognize comparable diameter sizes that can be used in instance in which the sleeve is made of a polymeric or other non-filament material. The sleeve can have a length in the range of about 10 centimeters to about 60 centimeters, and in one embodiment it has a length of about 40 centimeters.

A person having skill in the art will recognize that the configurations of FIGS. 1-3D are just some options for forming snare assemblies. In the illustrated embodiment the snare assembly is made of a single filament. In other embodiments, however, multiple filaments can be used, for example by using one filament to create a component that includes a snare, such as a snare linkage, and another filament to form a collapsible loop in place of a terminal end (e.g., terminal end 24 shown in FIG. 1), as described in more detail in U.S. patent application Ser. No. 13/465,288 filed concurrently herewith, and entitled "Systems, Devices, and Methods for Securing Tissue", the content of which is incorporated by reference herein in its entirety. Other exemplary embodiments of snare assemblies that can be used in conjunction with the teachings herein are described at least in U.S. patent application Ser. No. 13/218,810 filed Aug. 26, 2011, and entitled "SURGICAL FILAMENT SNARE ASSEMBLIES," the content of which is also incorporated by reference herein in its entirety.

Embodiments of surgical soft tissue repair devices described herein generally couple a snare assembly to a soft anchor. Soft anchors are generally flexible in nature and can be formed from a flexible filament or from a polymeric material in the form of, for example, a sleeve. Such soft anchors, which typically are non-metallic, can include one or more openings to allow at least a portion of the snare assembly to pass into and/or through the anchor. Soft anchors can have an unsettled or unstressed configuration that can be used for deployment to the surgical site, and an, anchoring configuration that can be used for fixating the anchor following deployment at the surgical site. Manipulation of the soft anchors can be effective to transition the anchors from the first, unstressed configuration to the second, anchoring configuration. The transition of a soft anchor from one configuration to the other typically alters the dimensions (e.g., the length and/or diameter) of the anchor. By way of a non-limiting example, in some repair device embodiments a diameter of a soft anchor in its anchoring configuration (i.e., its second diameter) can be in the range of about 10% greater to about 80% greater than the diameter in the unstressed configuration (i.e., its first diameter). In one embodiment, the second diameter can be about 20% greater than the first diameter of the soft anchor. Similarly, by way of further non-limiting example, in some repair device embodiments a length of a soft anchor in its anchoring configuration (i.e., its second length) can be in the range of about 20% less to about 80% less than a length of the soft anchor in its unstressed configuration (i.e., its first length). In one embodiment the second length can be about 50% less than the first length.

FIG. 4 illustrates one exemplary embodiment of a surgical soft tissue repair device 310 in which the snare assembly 20 from FIG. 1 is coupled to one embodiment of a soft anchor 312. As shown, the anchor 312 can be a cannulated suture 314 having a central lumen 316 disposed therethrough. The snare assembly 20 can pass through at least a portion of the central lumen 316 to couple the snare assembly 20 to the anchor 312 such that the anchor 312 is at an intermediate location on the snare assembly 20 (i.e., at a location between the first end 22 and the terminal end 24). More particularly, suture 312 can include a plurality of openings 318, 319 formed therein to accommodate coupling to the snare assembly and actuation of the anchor from the unstressed to the anchoring configuration. In the illustrated embodiment two openings are present in proximity to opposite ends of the anchor 312 for passing the snare assembly into and out of the central lumen 316. One skilled in the art will appreciate that the openings 318, 319 can be located in a number of different locations. In the illustrated embodiment the first opening 318 is formed in proximity to a proximal portion 312p of the anchor 312 and the second opening 319 is formed in proximity to a proximal portion 312d of the anchor 312. As shown, the first and second openings 318, 319 face each other, but if the cannulated suture 314 was stretched out into an approximately straight line, it could be said that the openings 318, 319 are located on the same side of the soft anchor 312.

As noted above, once deployed in bone the anchor 312 is capable of moving between a first, unstressed configuration and a second, anchoring configuration. The placement of the soft anchor 312 in bone, as will be explained below, causes the anchor to be laterally constrained within a bore that is formed in bone. When tension is applied to the snare assembly, which is coupled to the soft anchor, the soft anchor deforms. This deformation causes the dimensions of the anchor to be altered. As the diameter of the deployed anchor increases within the bore in which it is deployed, as explained above, the length decreases. The effect of the increasing diameter is to create a frictional engagement of the soft anchor within the bore and/or fixation of portions of the anchor into bone (particularly cancellous bone), thereby fixating the anchor in bone and allowing tissue attached to the snare assembly to be secured in a desired position.

The anchor 312 can be made of a variety of materials in a variety of forms. In one exemplary embodiment the anchor 312 is formed using a surgical filament, such as a cannulated filament or a braided filament. Alternatively, the anchor 312 can be made from a polymeric material in the form of a flexible sleeve. The type, size, and strength of the materials used to form the soft anchor 312 can depend, at least in part, on the other materials that form the snare assembly, the type of tissue in which it will be deployed, and the type of procedure with which it will be used. In one exemplary embodiment the anchor is formed from a #2 filament (about 23 gauge to about 24 gauge), such as an Orthocord™ filament that is commercially available from DePuy Mitek, Inc. or an Ethibond™ filament that is commercially available from Ethicon, Inc., Route 22 West, Somerville, N.J. 08876. The cores of these filaments can be removed to form the cannulated configuration. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

A length of the anchor when it is in an approximately linear, unfolded and undeployed configuration can be in the range of about 8 millimeters to about 50 millimeters, and in one embodiment it can be about 20 millimeters. Further, a length of the anchor when it is deployed and in its unstressed configuration (FIG. 5A, described below) can be in the range of about 4 millimeters to about 25 millimeters, and in one embodiment it can be about 10 millimeters and a diameter of the deployed soft anchor in such a configuration (i.e., a folded configuration) can be in the range of about 0.5 millimeters to about 5 millimeters, and in one embodiment it can be about 1 millimeter. Still further, a length of the anchor when it is deployed and in its anchoring configuration (FIG. 5B, described below) can be in the range of about 2 millimeters to about 25 millimeters, and in one embodiment it can be about 5 millimeters and a diameter in such a configuration can be in the range of about 1 millimeter to about 10 millimeters, and in one embodiment it can be about 2 millimeters.

A person having skill in the art will recognize a variety of other constructions the device 310, the snare assembly 20 (discussed above), and the anchor 312 can have without departing from the spirit of the present disclosure. By way of non-limiting examples, the snare assembly 20 can be coupled to the anchor 312 at different locations than illustrated, can pass in and out of the cannulated suture 314 any number of times, the suture 314 can have a twisted configuration, and openings 318, 319 for allowing the snare assembly to pass into the central lumen 316 can be relocated to other portions of the anchor 312. A person having skill in the art will recognize the way by which the snare assembly 20 is passed through and across the anchor 312 can affect the look and performance of the second, anchoring configuration. Other anchors with which the snare assembly 20 can be coupled to and operated similar to manners provided for herein are described at least in U.S. Pat. No. 7,658,751 to Stone et al., the content of which is incorporated by reference herein in its entirety.

FIGS. 5A-5H illustrate one exemplary method for performing a tissue repair using the repair construct illustrated in FIG. 4. A surgical opening can be formed through skin 1000 and a cannula can be passed therethrough to access a surgical repair site in a manner well known to those skilled in the art. Although cannulas are often used to define a channel through which the procedure can be performed, the cannula is not shown in FIGS. 5A-5H for ease of illustration. Accordingly, to the extent the figures show components of the systems and devices passing through skin 1000, these components would typically be extending through the cannula, which itself is passed through the skin 1000. Further, although the devices and methods described herein are particularly useful for minimally invasive surgery, such as arthroscopic surgery, they can also be used in open surgical procedures.

As shown in FIG. 5A, the snare assembly 20 can be coupled to the anchor 312 by passing the terminal end 24 through the opening 318, through the central lumen 316, and out the other opening 319 so that the anchor 312 is located at an intermediate location of the snare assembly 20 with the snare 30 extending from a first side of the anchor 312 and the terminal end 24 extending from the other. A bore 1002 can be formed in a bone 1001 and the device 310 shown in FIG. 4 can be inserted into the bore. In the deployed, unstressed configuration shown in FIG. 5A, the anchor is folded essentially in half to assume a U-like shape. Alternatively, the anchor can be delivered in an unfolded, e.g., approximately straight, configuration.

One skilled in the art will appreciate that a number of different techniques can be used to place the device 310 into the bore. By way of non-limiting example, the anchor 312 can be coupled to a distal end of a stiff wire or other similar tool or device to position the anchor 312 within the bore 1002. The wire can have one or more prongs at its distal end, thereby forming a fork, and the anchor 312 can be wrapped through one or more of the one or more prongs such that the anchor 312 remains in its unstressed configuration during insertion. Alternatively, the wire can have a single prong at its distal end such the prong pierces through the anchor, similar to a skewer. In other embodiments, the wire can include one or more slanted cuts on a side of the wire near its distal end, and the anchor 312 can be hung into one or more of the one or more slanted cuts. By way of further non-limiting example, the anchor 312 can be located in a device or tool similar to the device 590 described below with respect to FIG. 9A and placed in the bore 1002 in a similar manner. By way of one final non-limiting example, the anchor 312 can include a fish tail like the fish tail 617 described below with respect to FIGS. 10 and 11A-11J and inserted into bone 1001 in a similar manner.

As shown in FIG. 5B, after the anchor is deployed, tension can be applied to the snare assembly 20 approximately in a direction C, which in turn can actuate the anchor 312 to move from its unstressed configuration to its anchoring configuration. This tension causes deformation of the anchor 312 and it substantially bunches and has a greater diameter in the anchoring configuration. In the illustrated embodiment the bunched, anchoring configuration is substantially W-shaped for illustrative purposes, but a person skilled in the art will recognize a number of different configurations that the anchor 312 can have in the anchoring configuration. In this configuration the anchor 312 engages and impinges the walls of the bore 1002, penetrating cancellous bone in some embodiments so that the anchor 312 can be substantially fixed with respect to the bore 1002. While the overall shape of the anchor in the anchoring configuration will depend, at least in part, on the way the snare assembly 20 is coupled to the anchor 312, as shown the diameter of the anchor in the second, anchoring configuration increases in comparison to the diameter in the unstressed configuration, while the length of the anchor in the anchoring configuration decreases in comparison to the length of the unstressed configuration.

As described herein, the impingement of the anchor, such as the anchor 312 and the anchors 412, 512, 612 described below, into the walls of the bore 1002 may be initiated solely by friction between the anchor and the walls and further helped by varying bone density, which in general increases in a direction from the distal end of the bore 1002 to the proximal end. The shape transformation process may also be initiated by introducing a retaining device against the anchor and applying tension on the snare against the retaining device.

As shown in FIG. 5C, the terminal end 24 of the snare assembly 20 can be passed into and through at least a portion of the tendon 1003 detached from the bone 1001. Optionally, a needle or similar tool or device can be coupled to the terminal end 24 to assist with threading the snare assembly 20 through the tendon 1003. Likewise, other shuttling techniques known to a person skilled in the art can also be used to pass the snare assembly through the tendon.

As shown in FIGS. 5D and 5E, a portion of the terminal end 24 can be passed through the opening 32 of the snare 30 and the snare 30 can be collapsed or dressed in a manner consistent with its snare type. Thus, in the illustrated embodiment the snare 30 can be collapsed by moving the knot that forms the snare 30 away from the terminal end 24.

As shown in FIG. 5F, tension can be applied to the terminal end 24 by pulling approximately in a direction D, thereby causing the collapsed snare 30 to slide distally toward the tendon 1003 in a zip line-like manner until the snare 30 is adjacent to the tendon 1003. This, in turn, can cause the tendon 1003 to move toward and into contact with the bone 1001. Alternatively, tension can be applied to the terminal end 24 before the snare 30 is dressed and after the snare 30 is adjacent to the tendon 1003, or some combination of the two actions can be used, such as partially dressing the snare 30 before zip-lining it toward the tendon 1003. As shown in FIG. 5F, in embodiments that include the sleeve 50, as the snare is slid distally toward the tendon, the sleeve 50 can move proximally, out of the body. The sleeve 50, if included, can be removed at any time, as shown in FIG. 5G for example. Final tensioning can be carried out by applying tension to the terminal end 24, or the sleeve 50 if it remains associated with the snare assembly.

As shown in FIG. 5H, one or more half-hitches can be formed proximate to the collapsed snare to allow for incremental or ratchet-like tensioning and/or to maintain a location of the collapsed snare. After a first half-hitch is formed, the snare assembly 20 can be further tensioned in an incremental or ratchet-like manner by applying tension to the snare assembly 20. The addition of a second or more half-hitches can lock the location of the collapsed snare. Excess filament can then be trimmed and removed to complete the procedure. Other techniques known to those skilled in the art can be used to maintain the location of the collapsed snare, and thus the approximated tissue.

FIG. 6 illustrates another exemplary embodiment of a surgical soft tissue repair device 410 in which the snare assembly 20 from FIG. 1 is coupled to a soft anchor 412. As shown, the anchor 412 can be in the form of suture 414, or another flexible element such as a polymeric sleeve, having plurality of openings 416 formed therein with a plurality of bores 418 extending through the anchor 412 along a length thereof. The soft anchor 412 may be cannulated or non-cannulated. As illustrated, the snare assembly 20 can enter and exit the anchor 412 through the openings 416 and pass across the anchor 412 through the bores 418 to couple the snare assembly 20 to the anchor 412 such that the anchor 412 is at an intermediate location on the snare assembly 20. The openings 416 and bores 418 can be in a number of different configurations. In the illustrated embodiment, there are twelve openings 416 and six bores 418, with at least some of the bores 418 extending transversely between two openings 416. As shown, each opening 416 has a complimentary opening through the other side of the anchor 412, and a bore 418 extends between the opposed paired openings 416. Furthermore, as shown, the snare assembly 20 can be passed across the anchor 412 symmetrically, and thus the opposed paired openings 416 having a bore 418 extending therebetween can have a mirror-image counterpart opposed paired openings 416 and bore 418 extending therebetween. Once deployed, the anchor 412 is capable of moving between an unstressed configuration and an anchoring configuration.

The anchor 412 can be made of a variety of materials, but in one exemplary embodiment the anchor 412 is formed using a surgical filament, such as a cannulated filament, a braided filament, or a mono filament. Alternatively, the anchor 412 can be made from a polymeric material in the form of a flexible sleeve. The type, size, and strength of the filament can depend, at least in part, on the other materials that form the snare assembly, the type of tissue in which it will be deployed, and the type of procedure with which it will be used. In one exemplary embodiment the anchor is formed from a #2 filament (about 23 gauge to about 24 gauge), such as an Orthocord™ filament that is commercially available from DePuy Mitek, Inc. or an Ethibond™ filament that is commercially available from Ethicon, Inc.

A length of the anchor when it is in an approximately linear, unfolded and undeployed configuration can be in the range of about 8 millimeters to about 50 millimeters, and in one embodiment it can be about 20 millimeters. Further, a length of the anchor when it is deployed and in its unstressed configuration (FIG. 7A, described below) can be in the range of about 4 millimeters to about 25 millimeters, and in one embodiment it can be about 10 millimeters and a diameter of the deployed soft anchor in such a configuration (i.e., a folded configuration) can be in the range of about 0.5 millimeters to about 5 millimeters, and in one embodiment it can be about 1 millimeter. Still further, a length of the anchor when it is deployed and in its anchoring configuration (FIG. 7B, described below) can be in the range of about 2 millimeters to about 10 millimeters, and in one embodiment it can be about 5 millimeters and a diameter in such a configuration can be in the range of about 1 millimeter to about 10 millimeters, and in one embodiment it can be about 2 millimeters.

A person having skill in the art will recognize a variety of other constructions the device 410, the snare assembly 20 (discussed above), and the anchor 412 can have without departing from the spirit of the present disclosure. By way of non-limiting example, any number of openings and bores, and configurations thereof, can be used, although in some embodiments the number of bores can be in the range of about 2 bores to about 10 bores, and in one embodiment there can be 4 bores while in another embodiment there can be 6 bores. Further, the anchor 412 can be configured to allow the snare assembly 20 to pass through any portion thereof, including in an asymmetric and non-transverse manner, depending, at least in part, on other components of the device 410 and the desired second, anchoring configuration, among other factors. A person having skill in the art will recognize that the way in which the snare assembly 20 is passed through and across the anchor 412 can affect the look and performance of the anchoring configuration. Other anchors with which the snare assembly 20 can be coupled to and operated similar to manners provided for herein are described at least in literature related to the Y-KNOT® suture anchor systems that are commercially available from CONMED, 525 French Road Utica, NY 13502, the content of which is incorporated by reference herein in its entirety.

FIGS. 7A-7H illustrate one exemplary method for performing a tissue repair using the repair construct illustrated in FIG. 6. A surgical opening can be formed through skin 1000 and a cannula can be passed therethrough to access a surgical repair site according to well known techniques. Similar to FIGS. 5A-5H, although cannulas are often used to define a channel through which the procedure can be preformed, the cannula is not shown in FIGS. 7A-7H for ease of illustration. Accordingly, to the extent the figures show components of the systems and devices passing through skin 1000, these components would typically be extending through the cannula, which itself is passed through the skin 1000.

Figure 7A:
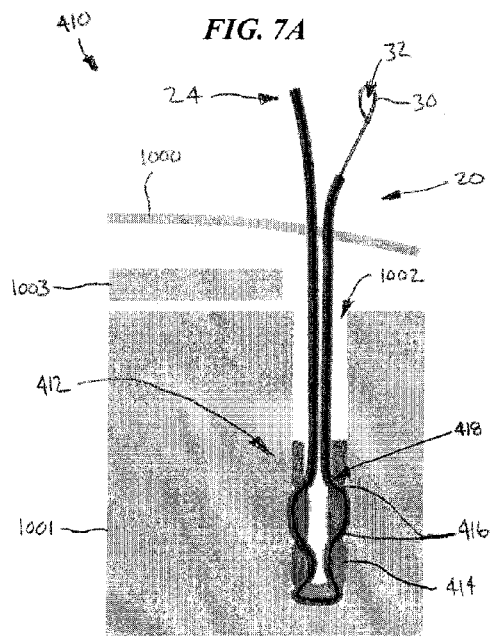

As shown in FIG. 7A, the snare assembly 20 can be coupled to the anchor 412 by passing the terminal end 24 through and across the openings 416 and the bores 418 formed therein so that the anchor 412 is located at an intermediate location of the snare assembly 20 with the snare 30 extending from a first side of the anchor 412 and the terminal end 24 extending from the other. A bore 1002 can be formed in a bone 1001 and the device 410 shown in FIG. 6 can be inserted into the bore, for instance in a folded configuration as shown or in an unfolded, e.g., approximately straight, configuration. A number of different techniques can be used to place the device 410 into the bore, including techniques known to those skilled in the art, those described above with respect to the anchor 312, and those described below with respect to FIGS. 9A, 10, and 11A-11J. By way of non-limiting example, a device having a plurality of prongs can be used to insert the anchor 412 such that the prongs maintain the anchor 412 in its first, unstressed configuration during insertion.

Figure 7B:
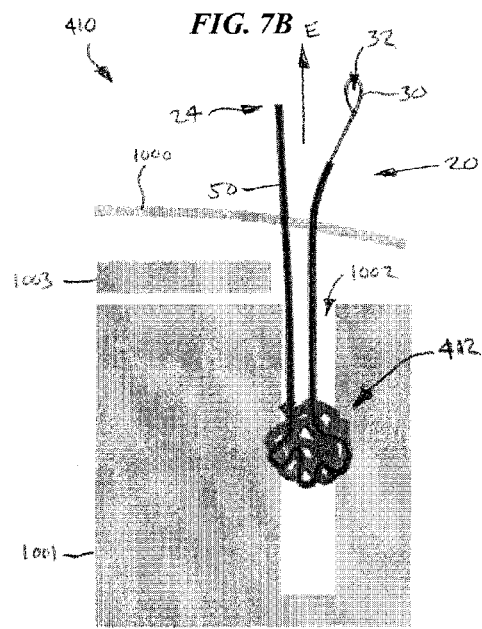
Figure 7C:
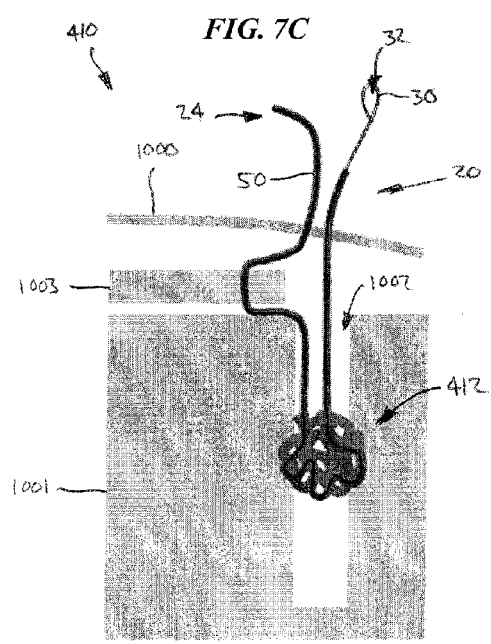
Figure 7D:
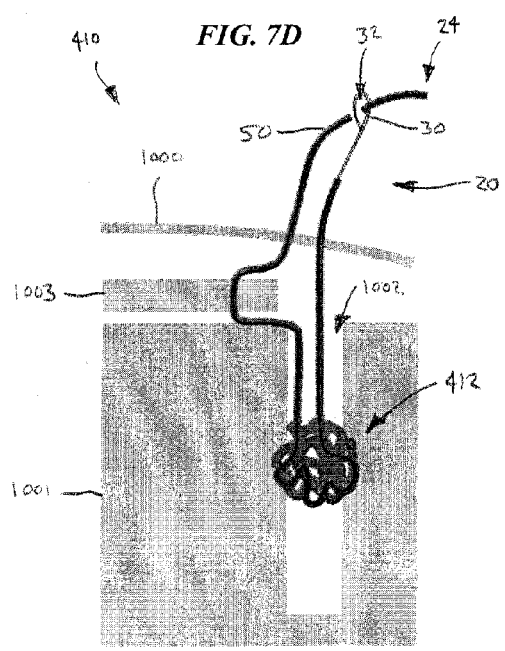

As shown in FIG. 7B, after the anchor is deployed in bone, tension can be applied to the snare assembly 20 approximately in a direction E, which in turn can actuate the anchor 412 to move from its unstressed configuration to its anchoring configuration. This tension causes deformation of the anchor 412 and it substantially bunches and has a greater diameter in the anchoring configuration. In the illustrated embodiment the bunched, anchoring configuration is substantially fist-like or spherical for illustrative purposes, but a person skilled in the art will recognize a number of different configurations that the anchor 412 can have in the anchoring configuration. In this configuration the anchor 412 engages and impinges the walls of the bore 1002 in its anchoring configuration, penetrating cancellous bone in some embodiments so that the anchor 412 can be substantially fixed with respect to the bore 1002. While the overall shape of the anchor in the anchoring configuration will depend, at least in part, on the way the snare assembly 20 is coupled to the anchor 412, as shown the diameter of the anchor in the second, anchoring configuration increases in comparison to the diameter in the unstressed configuration, while the length of the anchor in the anchoring configuration decreases in comparison to the length of the unstressed configuration.

The device 410 can then be operated in a manner similar to as described with respect to FIGS. 5C-5H. Thus, at least a portion of the terminal end 24 can be passed through at least a portion of the tendon 1003 and through the opening 32 in the snare 30 and the snare 30 can be collapsed or dressed, for instance by moving the knot that forms the snare 30 away from the terminal end 24. The snare 30 can be slid distally toward the tendon 1003 by applying tension approximately in a direction F, which can result in the snare 30 being adjacent to the tendon 1003 and the tendon 1003 moving towards the bone 1001. Final tensioning and removal of the sleeve 50, if used, can occur, and one or more half-hitches can be formed proximate to the collapsed snare 30 to allow for incremental or ratchet-like tensioning and/or to maintain a location thereof. Excess filament can then be trimmed and removed to complete the procedure.

FIG. 8 illustrates yet another exemplary embodiment of a surgical soft tissue repair device 510 in which the snare assembly 20 from FIG. 1 is coupled to the anchor 512. As shown, the anchor 512 can be a crocheted suture 514 having a plurality of openings 516 defined between filament limbs along a length thereof. The snare assembly 20 can be woven back-and-forth across the suture 514 any number of times to couple the snare assembly 20 to the anchor 512 such that the anchor 512 is at an intermediate location on the snare assembly 20. In the illustrated embodiment the snare assembly is passed across the suture 514 at a proximal end 514p of the suture 514 and is passed back-and-forth across the suture 514 five more times, each time being more distal of the next, before being looped back from a distal end 514d to the proximal end 514p and being passed across the suture 514 one last time at the proximal end 514p.

The anchor 512 can be made of a variety of materials, but in one exemplary embodiment the anchor 512 is formed using a surgical filament, such as a cannulated filament, a braided filament, or a mono filament. The type, size, and strength of the filament can depend, at least in part, on the other materials that form the snare assembly, the type of tissue in which it will be deployed, and the type of procedure with which it will be used. In one exemplary embodiment the anchor is formed from a #2 filament (about 23 gauge to about 24 gauge), such as an Orthocord™ filament that is commercially available from DePuy Mitek, Inc. or an Ethibond™ filament that is commercially available from Ethicon, Inc.

The length of the anchor 512 when it is deployed in bone and in its unstressed configuration (FIG. 9A, described below) can be in the range of about 5 millimeters to about 50 millimeters, and in one embodiment it can be about 25 millimeters. The diameter of anchor 512 in such a configuration can be in the range of about 0.5 millimeters to about 5 millimeters, and in one embodiment it can be about 1 millimeter. When the anchor 512 is deployed and in its anchoring configuration (FIG. 9B, described below), its length can be in the range of about 2 millimeters to about 10 millimeters, and in one embodiment it can be about 5 millimeters. The diameter of the deployed anchor 512 in its anchoring configuration can be in the range of about 1 millimeter to about 10 millimeters, and in one embodiment it can be about 2 millimeters.

A person having skill in the art will recognize a variety of other constructions the device 510, the snare assembly 20 (discussed above), and the anchor 512 can have without departing from the spirit of the present disclosure. By way of non-limiting example, the snare assembly 20 can be passed across the anchor 514 any number of times at any number of locations, and not necessarily in a consecutive downstream or upstream order. A person having skill in the art will also recognize that the way by which the snare assembly 20 is passed through and across the anchor 512 can affect the look and performance of the second, anchoring configuration. Other anchors to which the snare assembly 20 can be coupled to and operated similar to manners provided for herein are described at least in U.S. Patent Application Publication No. 2011/0022083 filed Jul. 24, 2009, and entitled "METHODS AND DEVICES FOR REPAIRING AND ANCHORING DAMAGED TISSUE," the content of which is incorporated by reference herein in its entirety.

FIGS. 9A-9H illustrate one exemplary method for performing a tissue repair using the repair construct illustrated in FIG. 8. A surgical opening can be formed through skin 1000 and a cannula can be passed therethrough to access a surgical repair site according to well known techniques. Similar to FIGS. 5A-5H, although cannulas are often used to define a channel through which the procedure can be preformed, the cannula is not shown in FIGS. 9A-9H for ease of illustration. Accordingly, to the extent the figures show components of the systems and devices passing through skin 1000, these components would typically be extending through the cannula, which itself is passed through the skin 1000.

As shown in FIG. 9A, the snare assembly 20 can be coupled to the anchor 512 in a manner similar to that described above with respect to FIG. 8. This construction is such that the anchor 512 is located at an intermediate location of the snare assembly 20 with the snare 30 extending from a first side of the anchor 512 and the terminal end 24 extending from the other. A bore 1002 can be formed in a bone 1001 and the device 510 shown in FIG. 8 can be inserted into the bore. A number of different techniques can be used to place the device 510 into the bore, including techniques known to those skilled in the art. By way of non-limiting example, an insertion device 590 having a body 592 defining a cavity 594 therein and a piston 596 disposed within the cavity 594 can be inserted to a distal end 1002*d* of the bore 1002 so that the anchor 512 is located distally within the bore 1002, as shown in FIG. 9A. The device 590 can also include one or more features to manage the snare assembly 30, including, by way of non-limiting example, a central lumen 598 in the piston 596 for receiving the snare assembly 20. The body 592 can be removed while the piston 596 is left stationary to hold the anchor 512 in place, and then after the body 592 is removed, the piston 596 can be removed, thereby leaving the anchor 512 disposed in the bore 1002. Such a configuration allows unintended movement of the anchor 512 to be minimized or eliminated, thereby reducing the possibility of a premature deployment to the second, anchoring configuration. In an alternative embodiment, the device 590 can be located adjacent to a proximal end 1002*p* of the bore 1002 and the piston 596 can be actuated to move the anchor 512 from the device 590 and into the bore 1002. Still further, delivery options discussed above with respect to the anchors 312, 412 can also be used with the anchor 512, as well as other techniques known to those skilled in the art.

With reference to FIG. 9B, once the anchor 512 is disposed in bore 1002 tension can be applied to the snare assembly 20 approximately in a direction G. With the anchor constrained within bore 1002, this force actuates the anchor 512 so that it transitions from its unstressed configuration to its anchoring configuration. This tension causes deformation of the anchor 512 and it substantially bunches and has a greater diameter in the anchoring configuration. In the illustrated embodiment the bunched, anchoring configuration substantially fist-like or spherical for illustrative purposes, but a person skilled in the art will recognize a number of different configurations that the anchor 512 can have in the anchoring configuration. In this configuration the anchor 512 engages and impinges the walls of the bore 1002, penetrating cancellous bone in some embodiments so that the anchor 512 can be substantially fixed with respect to the bore 1002. While the overall shape of the anchor in the anchoring configuration will depend, at least in part, on the way the snare assembly 20 is coupled to the anchor 512, as shown the diameter of the deployed anchor in 512 the anchoring configuration increases in comparison to the anchor diameter of the unstressed configuration, while the length of the deployed anchor in the anchoring configuration decreases in comparison to the diameter of the anchor in the unstressed configuration.

As described above, the impingement of the anchor into the walls of the bore 1002 may be initiated solely by friction between the anchor and the walls and further helped by varying bone density, and further, the shape transformation process may also be initiated by introducing a retaining device against the anchor and applying tension on the snare against the retaining device. In some embodiments, the piston 596 can serve as the retaining device. For example, after the body 592 is retracted, the piston 596 can be kept in place and the snare assembly 20 can be tensioned against the piston 596, thus causing the anchor 512 to move to the anchoring configuration. The piston 596 can then be removed from the surgical site. In such embodiments the lumen 598 of the piston 596 can be small enough so as not to accommodate the snare assembly 20 and the anchor 512 together.

Following deployment of the anchor 512 from its first, unstressed configuration to its second, anchoring configuration, the device 510 can be operated in a manner similar to that described with respect to FIGS. 5C-5H. Thus, at least a portion of the terminal end 24 can be passed through at least a portion of the tendon 1003 and through the opening 32 in the snare 30 and the snare 30 can be collapsed or dressed, for instance by moving the knot that forms the snare 30 away from the terminal end 24. The snare 30 can be slid distally toward the tendon 1003 by applying tension approximately in a direction H, which can result in the snare 30 being adjacent to the tendon 1003 and the tendon 1003 moving toward the bone 1001. Final tensioning and removal of the sleeve 50, if used, can occur, and one or more half-hitches can be formed proximate to the collapsed snare 30 to allow for incremental or ratchet-like tensioning and/or to maintain a location thereof. Excess filament can then be trimmed and removed to complete the procedure.

FIG. 10 illustrates still another exemplary embodiment of a surgical soft tissue repair device 610 in which the snare assembly 20 of FIG. 1 is coupled to soft anchor 612. As shown, the anchor 612 is of a similar nature as the anchor 512, and thus it can include the same features discussed above with respect to the anchor 512. Accordingly, it can be a crocheted suture 614 having a plurality of openings 616 defined between filament limbs along a length thereof, with the snare assembly being woven back-and-forth across the suture 614 in a manner similar as described above such that the anchor 612 is at an intermediate location on the snare assembly 20. The anchor 612 includes a fish tail 617 at a distal end 614d of the suture 614. The fish tail 617 can be used to assist with inserting the anchor 612 to a surgical site, as discussed in greater detail below. In particular, fish tail 617 can assist in navigating the device through and around obstructions and various non-linear paths in the body. As shown, a needle 619 or other similar tool or device can optionally be coupled to the suture 612 to assist with threading the fish tail 617 through obstructions, such as skin and tissue.

The materials and dimensions of the device 610 can likewise be similar to those discussed above with respect to the device 510, with the fish tail 617 being part of the suture 614. The length of the fish tail 617 can depend, at least in part, on the dimensions of the rest of the suture 614, other components with which it is being used, and the type of procedures with which it is being used. The fish tail 617 can have a length in the range of about 5 centimeters to about 100 centimeters, and in one embodiment a length of the fish tail is about 40 centimeters. A person having skill in the art will recognize a variety of other constructions the device 610, the snare assembly 20 (discussed above), and the anchor 612 can have without departing from the spirit of the present disclosure. Further, a person having skill in the art will recognize that a fish tail similar to the fish tail 617 can be incorporated in various other anchor embodiments, including but not limited to the anchors 312, 412, and 512 provided herein. The use of the fish tail to position such anchors would occur in a manner similar to the manner described below with respect to FIGS. 11A-11J.

FIGS. 11A-11J illustrate one exemplary method for performing a tissue repair using the repair construct illustrated in FIG. 10. A surgical opening can be formed through skin 1000 and a cannula can be passed therethrough to access a surgical repair site according to well known techniques. Similar to FIGS. 5A-5H, although cannulas are often used to define a channel through which the procedure can be preformed, the cannula is not shown in FIGS. 11A-11J for ease of illustration. Accordingly, to the extent the figures show components of the systems and devices passing through skin 1000, these components would typically be extending through the cannula, which itself is passed through the skin 1000.

As shown in FIG. 11A, the snare assembly 20 can be coupled to the anchor 612 in the same manner as described above with respect to FIG. 9A. Insertion of the device 610, however, can be different because of the fish tail 617. In one exemplary embodiment for insertion of the device 610 to a surgical site, a bore 1002 is formed fully through the bone 1001 and the fish tail 617 is used as a shuttle to bring the anchor 612 to the desired location. In the illustrated embodiment the fish tail 617 passes through a top layer of skin 1000, through the bore 1002, and out of a bottom layer of skin 1000. As shown in FIG. 11B, tension can be applied to the fish tail 617 in approximately a direction J to pull the anchor 612 through the bore 1002 and to the desired location. The snare assembly 20 can be used to counteract the force applied by the fish tail 617 by delivering a force in a direction approximately opposite to the direction J to assist in placement of the device 610. Although in the illustrated embodiment the fish tail 617 extends through the bottom layer of skin 1000, in other embodiments it can remain in the body but be just distal of the bore 1002, which still allows tension to be applied thereto to help shuttle the anchor 612 to the desired location.

Figure 11C:
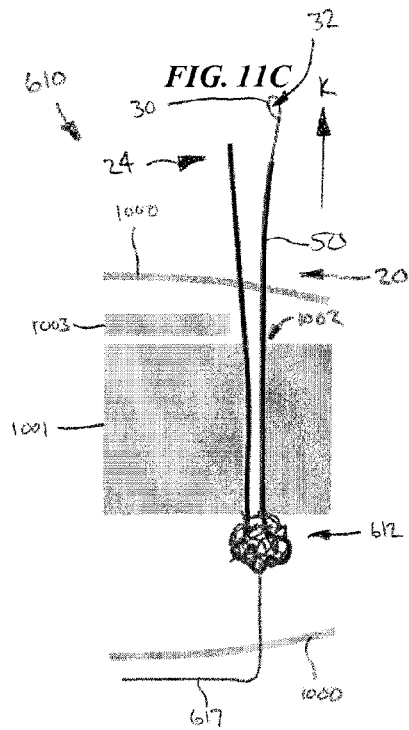
Figure 11D:
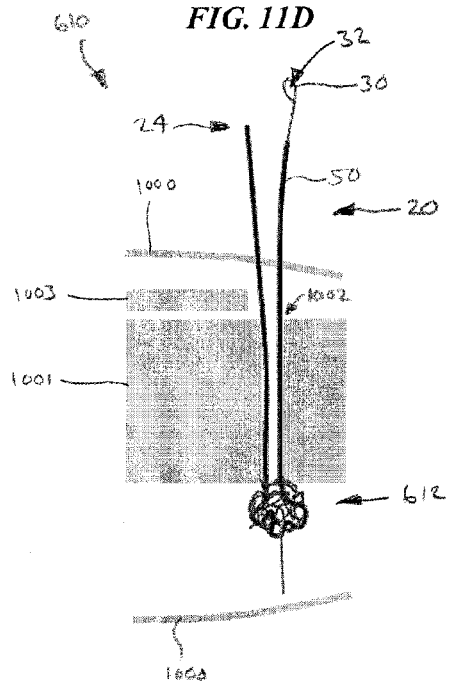
Figure 11E:
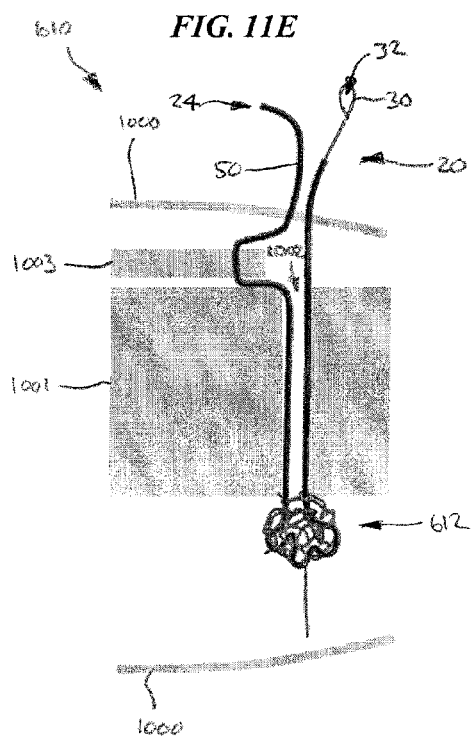
Figure 11F:
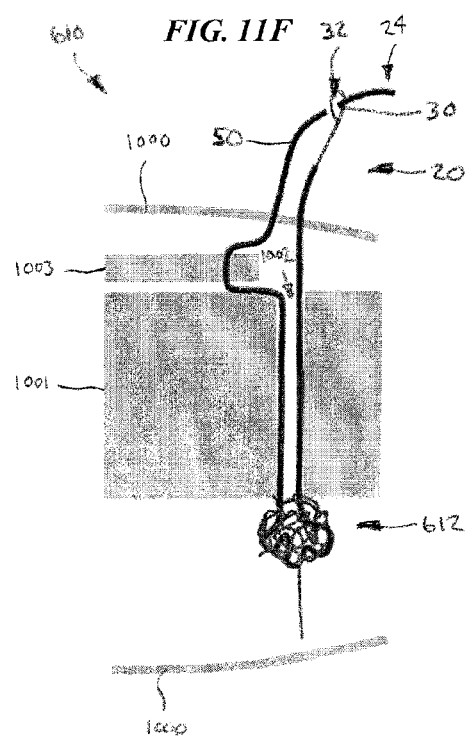
Figure 11G:
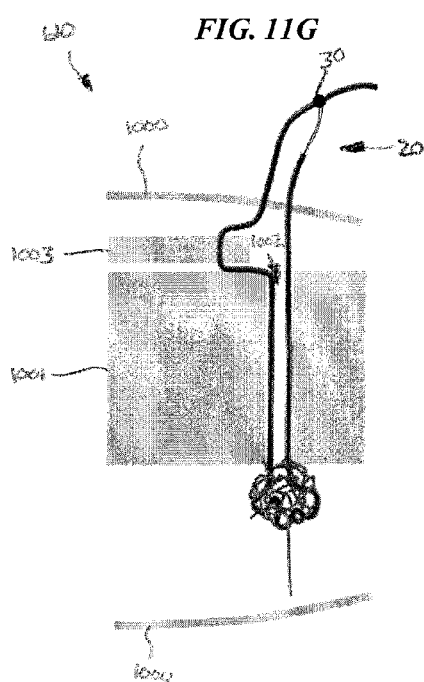
Figure 11H:
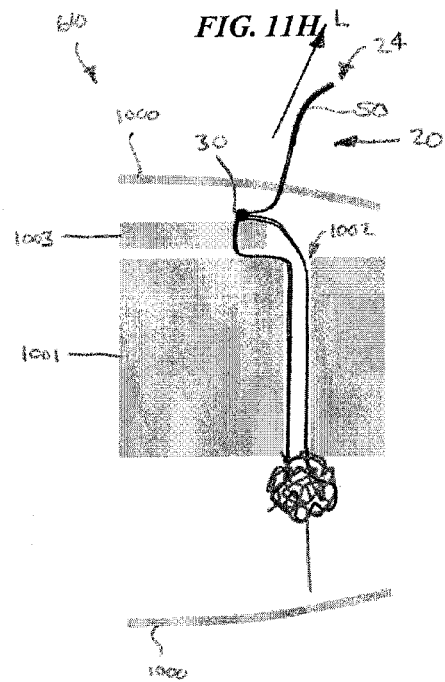
Figure 11I:
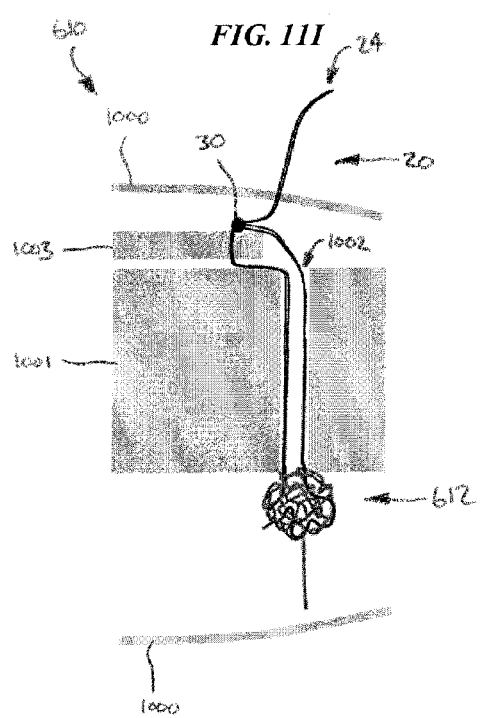
Figure 11J:
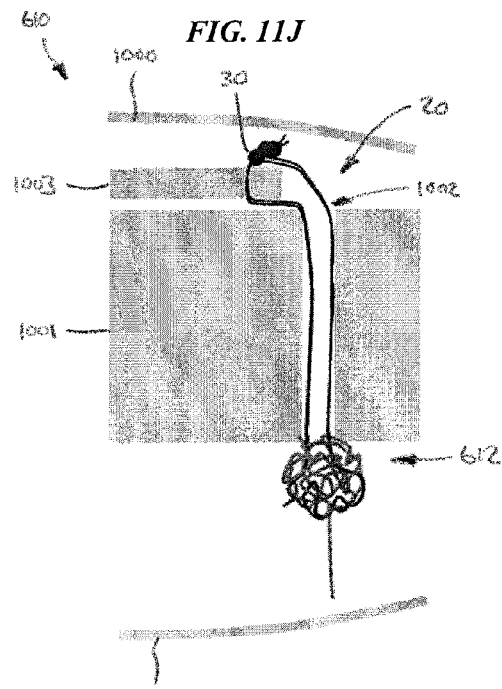

The device 610 can then be utilized in a manner similar to that described with respect to FIGS. 9B-9H. Thus, tension can be applied to the snare assembly 20 approximately in a direction K to move the anchor from its unstressed configuration to its anchoring configuration. This tension causes deformation of the anchor 612 and it substantially bunches and has a greater diameter in the anchoring configuration. Again, in the illustrated embodiment the bunched, anchoring configuration is substantially fist-like or spherical for illustrative purposes, but a person skilled in the art will recognize a number of different configurations that the anchor 612 can have in the anchoring configuration. When the anchor 612 is deployed and in its anchoring configuration, it typically resides just distal to bore 1002, on the side of the bore adjacent to the bottom layer of tissue. At least a portion of the terminal end 24 can be passed through at least a portion of the tendon 1003 and through the opening 32 in the snare 30 and the snare 30 can be collapsed or dressed, for instance by moving the knot that forms the snare 30 away from the terminal end 24. The snare 30 can be slid distally toward the tendon 1003 by applying tension approximately in a direction L, which can result in the snare 30 being adjacent to the tendon 1003 and the tendon 1003 moving toward the bone 1001. Final tensioning and removal of the sleeve 50, if used, can occur, and one or more half-hitches can be formed proximate to the collapsed snare 30 to allow for incremental or ratchet-like tensioning and/or to maintain a location thereof. Excess filament can then be trimmed and removed to complete the procedure. The fish tail 617 can also be trimmed and removed. Although removal of the fish tail 617 is illustrated in FIG. 11D, such removal can occur at any time after the anchor 612 is shuttled to its desired location.

A person skilled in the art will recognize a number of different modifications that can be made to the soft anchor procedures discussed herein without departing from the spirit of the invention. By way of one non-limiting example, although the embodiments herein illustrate the snare assembly 20 passing through tissue at one location, in other embodiments, it can pass through two or more locations and/or two or more tissues. By way of further non-limiting example, the snare assembly 20 can be coupled to tissue using a variety of techniques, for instance wrapping a portion of the snare assembly 20 around the tissue. By way of still a further non-limiting example, a snare 30 can be passed through tissue instead of or in addition to passing the terminal end 24 through tissue. A pin or other fixation element can be placed across any coaxial sliding neck of the snare to prevent unintentional collapse in such an embodiment, or could be included in any snare assembly embodiment for extra precaution. Still further, a person having skill in the art will recognize that the order of at least some of the method steps provided herein can be altered without departing from the spirit of the present disclosure.

Additionally, the procedures discussed with respect to FIGS. 4-11G are just some forms of procedures that can be performed in conjunction with systems, devices, and methods disclosed herein. A person skilled in the art will recognize a number of other ways that the disclosed systems, devices, and methods can be used in various other configurations and types of surgical procedures. For instance, the systems, devices, and methods disclosed herein can easily be adapted to be used in conjunction with three or more components, such as multiple tissues and a bone or three or more soft tissues. Some non-limiting examples of other systems, devices, assemblies, constructs, and surgical procedures with which the present systems, devices, and methods can be used are described in U.S. patent application Ser. No. 13/218,810 filed Aug. 26, 2011, and entitled "SURGICAL FILAMENT SNARE ASSEMBLIES," and in U.S. patent application Ser. No. 13/465,288 filed concurrently herewith, and entitled "Systems, Devices, and Methods for Securing Tissue" the content of which was previously incorporated by reference herein in their entireties.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A surgical repair method, comprising:
    inserting a flexible anchor into a hole in a bone at a location proximate to detached soft tissue, the anchor having a first configuration with a first length and a first diameter and a second configuration with a second length that is less than the first length and a second diameter that is greater than the first diameter, the anchor being coupled to a snare assembly that passes through at least a portion of the anchor, the snare assembly being formed by an elongate filament having a collapsible snare at one end thereof and at least one filament tail extending therefrom, the at least one filament tail having a terminal end opposite the collapsible snare and the anchor being disposed on the at least one filament tail a distance away from a portion of the elongate filament that forms the collapsible snare;
    tensioning the elongate filament to move the anchor from the first configuration to the second configuration to fix the anchor relative to the bone;
    passing at least one of the snare and the terminal end of the at least one filament tail through at least a portion of the detached soft tissue;
    inserting the terminal end of the at least one filament tail through the snare;
    collapsing the snare around the at least one filament tail; and
    sliding the collapsed snare toward the soft tissue to apply tension to portions of the elongate filament located between the anchor and the tissue so as to bring the tissue into proximity with the bone,
    wherein the portion of the elongate filament that forms the collapsible snare comprises first and second filament limbs that each extend in a first direction from a slidable knot that defines the collapsible snare, the first and second limbs each forms its own opening of the collapsible snare.

2. The method of claim 1, wherein the flexible anchor is a cannulated anchor with a lumen extending therethrough, the flexible anchor having a first opening at a proximal end and a second opening at a distal end, each of the first and second openings communicating with the lumen.

3. The method of claim 1, wherein the flexible anchor has a plurality of bores extending transversely therethrough along the length of the flexible anchor.

4. The method of claim 1, wherein the second diameter is at least about 20% greater than the first diameter.

5. The method of claim 1, wherein the second length is at least about 50% less than the first length.

6. The method of claim 1, wherein first and second filament limbs each extend from the slidable knot in a second opposite direction, away from the collapsible snare, to form the at least one filament tail that extends from the collapsible snare.

7. The method of claim 6, wherein a flexible sleeve removably encapsulates at least a portion of the first and second limbs that form the at least one filament tail.

8. The method of claim 7, further comprising:
    removing the sleeve from the portion of the first and second limbs that the sleeve encapsulates.

9. The method of claim 1, wherein the collapsible snare is located on a terminal end of the elongate filament.

10. A surgical method, comprising:
    inserting a flexible anchor into a hole in a bone at a location proximate to detached soft tissue, the anchor having a first configuration with a first length and a first diameter and a second configuration with a second length that is less than the first length and a second diameter that is greater than the first diameter, the anchor being coupled to a snare assembly that passes through at least a portion of the anchor, the snare assembly having a slidable knot having on one side thereof a cinch noose loop defined by a first filament and a second filament, the first and second limbs each forms its own opening of the collapsible snare, the slidable knot having on the other side thereof first and second filament limbs, the first and second filament limbs having terminal ends that extend freely from the slidable knot,
    tensioning at least one of the first and second filament limbs to move the anchor from the first configuration to the second configuration to fix the anchor relative to the bone;
    passing at least one of the snare and the terminal ends of the first and second filament limbs through at least a portion of the detached soft tissue;
    inserting the terminal ends of the first and second filament limbs through the cinch noose loop;
    collapsing the cinch noose loop around the first and second filament limbs; and
    sliding the collapsed cinch noose loop toward the soft tissue to apply tension to the first and second filament limbs located between the anchor and the tissue so as to bring the tissue into proximity with the bone.

11. The method of claim 10, wherein the slidable knot is formed by the first and second filament limbs and a flexible sleeve removably encapsulates at least a portion of the first and second filament limbs.

12. The method of claim 10, wherein the slidable knot comprises a central opening and a plurality of secondary openings peripheral to the central opening, wherein the first and second filament limbs pass through the central opening.

13. The method of claim 10, wherein the slidable knot comprises a central opening and a plurality of secondary openings peripheral to the central opening, wherein the first filament limb passes through one of the central opening and one opening of the plurality of secondary openings, and the second filament limb passes through another of the central opening and one opening of the plurality of secondary openings.

14. The method of claim 10, wherein a flexible sleeve removably encapsulates at least a portion of the first and second filament limbs.

15. The method of claim 14, the method further comprising:
removing the sleeve from the portion of the first and second limbs that the sleeve encapsulates.

16. A surgical method, comprising:
inserting a flexible anchor into a hole in a bone at a location proximate to detached soft tissue, the anchor having a first configuration with a first length and a first diameter and a second configuration with a second length that is less than the first length and a second diameter that is greater than the first diameter, the anchor being coupled to a snare assembly that passes through at least a portion of the anchor, the snare assembly having a slidable knot having on one side thereof a cinch noose loop defined by a first filament and a second filament, the slidable knot having on the other side thereof first and second filament limbs, the first and second filament limbs having terminal ends that extend freely from the slidable knot,
tensioning at least one of the first and second filament limbs to move the anchor from the first configuration to the second configuration to fix the anchor relative to the bone;
passing at least one of the snare and the terminal ends of the first and second filament limbs through at least a portion of the detached soft tissue;
inserting the terminal ends of the first and second filament limbs through the cinch noose loop;
collapsing the cinch noose loop around the first and second filament limbs; and
sliding the collapsed cinch noose loop toward the soft tissue to apply tension to the first and second filament limbs located between the anchor and the tissue so as to bring the tissue into proximity with the bone,
wherein the slidable knot comprises a central opening and a plurality of secondary openings peripheral to the central opening, and
wherein the first filament limb passes through one of the central opening and one opening of the plurality of secondary openings, and the second filament limb passes through another of the central opening and one opening of the plurality of secondary openings.

17. The method of claim 16, wherein the slidable knot is formed by the first and second filament limbs and a flexible sleeve removably encapsulates at least a portion of the first and second filament limbs.

18. The method of claim 16, wherein the flexible anchor is a cannulated anchor with a lumen extending therethrough, the flexible anchor having a first opening at a proximal end and a second opening at a distal end, each of the first and second openings communicating with the lumen.

19. The method of claim 16, wherein the flexible anchor has a plurality of bores extending transversely therethrough along the length of the flexible anchor.

20. The method of claim 16, wherein the second diameter is at least about 20% greater than the first diameter.

21. The method of claim 16, wherein the second length is at least about 50% less than the first length.

22. The method of claim 16, wherein a flexible sleeve removably encapsulates at least a portion of the first and second filament limbs.

23. The method of claim 22, the method further comprising:
removing the sleeve from the portion of the first and second limbs that the sleeve encapsulates.

* * * * *